(12) United States Patent
Fein

(10) Patent No.: US 7,127,141 B2
(45) Date of Patent: Oct. 24, 2006

(54) NON-IMAGING OPTICAL CORNER TURNER

(75) Inventor: Michael E. Fein, Mountain View, CA (US)

(73) Assignee: Nellcor Puritan Bennett Inc., Pleasanton, CA (US)

( * ) Notice: Subject to any disclaimer, the term of this patent is extended or adjusted under 35 U.S.C. 154(b) by 0 days.

(21) Appl. No.: 10/970,606

(22) Filed: Oct. 20, 2004

(65) Prior Publication Data

US 2005/0084212 A1    Apr. 21, 2005

Related U.S. Application Data

(63) Continuation of application No. 08/988,479, filed on Dec. 10, 1997, now Pat. No. 6,819,687.

(51) Int. Cl.
*G02B 6/26* (2006.01)

(52) U.S. Cl. ............... 385/39; 372/6; 372/99; 385/31

(58) Field of Classification Search ............ 385/39, 385/31; 372/6, 99
See application file for complete search history.

(56) References Cited

U.S. PATENT DOCUMENTS

| | | | |
|---|---|---|---|
| 3,895,856 A | 7/1975 | Bickel | |
| 4,102,579 A * | 7/1978 | Stewart | 356/73.1 |
| 4,898,450 A | 2/1990 | Jannson et al. | |
| 5,080,940 A | 1/1992 | Kugimaya | |
| 5,121,404 A * | 6/1992 | Aoshima et al. | 372/75 |
| 5,175,780 A * | 12/1992 | Sano et al. | 385/47 |
| 5,430,620 A | 7/1995 | Li et al. | |
| 5,623,919 A | 4/1997 | Kelly | |
| 5,629,996 A | 5/1997 | Rizkin et al. | |
| 5,680,492 A | 10/1997 | Hopler et al. | |
| 5,727,108 A | 3/1998 | Hed | |
| 5,742,633 A | 4/1998 | Stone et al. | |
| 5,743,731 A | 4/1998 | Lares et al. | |
| 5,774,608 A * | 6/1998 | Allen et al. | 385/39 |
| 5,903,694 A | 5/1999 | Sugawara | |
| 5,917,972 A | 6/1999 | Davies | |
| 6,057,966 A | 5/2000 | Carroll et al. | |
| 6,075,801 A | 6/2000 | Tamanuki et al. | |

* cited by examiner

*Primary Examiner*—Minsun C H Harvey
*Assistant Examiner*—Dung(Michael) T. Nguyen
(74) *Attorney, Agent, or Firm*—Fletcher Yoder

(57) ABSTRACT

The present invention provides a device and method to efficiently turn light from an optical fiber around a corner while avoiding the frustrated-TIR loss that would occur if the fiber were bent. The invention uses non-imaging optics which efficiently deal with beam divergence half-angles less than 90°. By recognizing that most light from a fiber optic source will have a divergence half-angle of less than 90 degrees, a practical solution is achieved using non-imaging optics.

10 Claims, 19 Drawing Sheets

NON-IMAGING OPTICAL CORNER TURNER

FIELD OF THE INVENTION

The present invention relates to a device that changes the direction of a beam of light in a non-imaging application (i.e. an application in which the primary concern is to transport optical energy efficiently, with minimal loss of brightness, rather than to preserve an image). The device is particularly useful in changing the direction of light that is carried by optical fibers, although it may also be useful in any optical system requiring the redirection of a light beam. Examples of such systems are solid optical waveguide structures on planar substrates, hollow optical waveguide structures (such as those commonly used in carrying infrared laser beams for surgical applications) and systems using relay lenses, in which the light beam travels primarily in air rather than in a solid material.

BACKGROUND OF THE INVENTION

An optical fiber cannot be bent around a sharp angle because it will break and it will lose light because some of the light rays it is carrying will strike the cladding at less than the critical angle. The critical angle of an optical fiber is the angle of rays to the normal to the boundary of the fiber at which total internal reflection (TIR) begins to fail, so that the light internal to the fiber begins to exit through the cladding. When this occurs, the efficiency of transmission is significantly reduced. To turn a sharp corner and yet prevent substantial failure of TIR, the fiber can be cut and flat mirrors along with other optics can be used to redirect the light from one substantially-straight section of fiber to another substantially-straight section of fiber which is oriented in another direction. This method of redirecting light provides a break in the optical fiber and allows the light to be turned so it can again be sent down a second optical fiber or otherwise used.

A fiber optic sharp corner turner is desirable for certain applications of pulse oximetry where wires are undesirable, such as in Magnetic Resonance Interference (MRI) applications. Pulse oximetry is typically used to measure various blood flow characteristics including, but not limited to, the blood-oxygen saturation of hemoglobin in arterial blood, the volume of individual blood pulsations supplying the tissue, and the rate of blood pulsations corresponding to each heartbeat of a patient. Measurement of these characteristics has been accomplished by use of a non-invasive sensor which passes light through a portion of the patient's tissue where blood perfuses the tissue and photoelectrically senses the absorption of light in such tissue. The amount of light absorbed is then used to calculate the amount of blood constituent being measured. For measuring blood oxygen levels, sensors have been provided with light sources and photodetectors that are adapted to operate at two different wavelengths, in accordance with known techniques for measuring blood oxygen saturation using optical signals carried by optical fibers.

MRI exams are typically used to view the internal structure of the human body. Observation of these internal structures has been accomplished by use of a non-invasive magnetic resonance frequency which passes through the body to create an internal picture of the person. For measuring blood oxygen levels during these procedures, fiber-optic-coupled pulse oximeters have been provided since it is desirable in the MRI environment to avoid attaching metal wires to the patient. One reason for this is that the patient might be burned by the wires during the procedure, since the high electromagnetic fields of the MRI instrument can induce high currents in the wires. Ordinary pulse oximetry systems include semiconductor diodes closely-coupled to the patient (two or more of such diodes for light emission and at least one for light detection) and electrical wires to connect those semiconductor diodes to the instrument. A fiber optic pulse oximetry system, on the other hand, has light emission and detection means remote to the patient, and connects these means to the patient's tissue by way of optical fibers. Such a pulse oximeter enables physicians to take data without risk of harming the patient. In a fiber-coupled pulse oximeter, the "sensor" (that is attached to the patient), rather than comprising light emitting and detecting devices, may simply comprise an optical interface between a pair of optical fiber bundles and the patient's tissue, one fiber bundle for bringing light to the patient and one for carrying it away.

A pulse oximeter sensor may be attached at a number of locations, such as a finger. To avoid movement causing stress at the connection to the sensor, the connecting wires, fibers, or fiber bundles may be taped to the patient a short distance from the attachment site. This means that, if an optical fiber is used as a connector, it must run parallel to the patient, then make a sharp turn to deliver the light to the skin. A similar sharp turn would be required for a fetal application of pulse oximetry, where the connector needs to enter through the vagina, then may need to make a turn to direct light at the fetus. Other medical sensors may have similar requirements—for example, in a fiber-optic instrument designed to detect the vitality of dental pulp by sending light through a tooth, it is necessary for an optical fiber to enter the mouth, and for light leaving the end of the fiber to be redirected sharply so as to enter the tooth.

There are prior art optical devices which can achieve efficient corner turning but they use imaging optics and tend to be expensive and bulky. Imaging optics allow a one-to-one correspondence of points on the input object in the object plane to points on the output image in the image plane. Non-imaging optics provide for transmission of light from the input plane to the output plane, without the requirement for one-to-one correspondence of object and image points. Other prior art corner turning devices often require high Numerical Aperture (NA) imaging optics and tend to be expensive and lossy.

In one oximeter system described in U.S. Pat. No. 5,537,499, a probe with a flat reflector is used to redirect light at an angle lateral to the axis of the fiber bundle. This probe incorporates Fresnel light reflections from the optical fiber and air interface, directing them laterally into the fiber and capsule enclosing the end of the fiber without secondary light reflections and refractions. In U.S. Pat. No. 5,515,468, a connector system for coupling between a fiber optic transmission line and an opto-electronic device is disclosed. With this system, light is bent around a corner using flat mirrors, internally reflecting prisms, and lenses. U.S. Pat. No. 5,343,543 provides a directional indicator and methods of use which gives a surgeon visual feedback as to the direction of radiation to be emitted from a side-firing laser fiber when the distal end of the laser fiber is obscured from observation. With such a system, the laser core has an integral tilted mirror at one end to cause the emitted beam to be at an angle to the laser axis. In U.S. Pat. No. 5,152,296, a pair of finger cuffs that include an electrocardiographic electrode, a first radiation source and detector pair for blood pressure measurement, and a second radiation source and detector pair for blood oxygenation measurement are disclosed. In this setup, an optical system with various beam-splitters, lenses, optical fibers, and beam re-directors are used.

Non-imaging optics are a type of optics which have only begun to be understood within the last few decades. The state of the art of analyzing and designing such optics as of 1989 has been summarized in W. T. Welford and R. Winston, High Collection Nonimaging Optics, Academic Press, c. 1989, which is herein incorporated by reference for all purposes. At the time of publication of this text, no non-imaging corner turners were known.

Welford and Winston described (see their page 4) a distinction between two-dimensional and three-dimensional (2D and 3D) designs of non-imaging optics, a concept which will be used herein, in a generalized fashion.

2D corner turners are bounded by more-or-less complex curves in the plane of the bend. The three-dimensional shapes of 2D corner turners are generated by moving those curves perpendicular to themselves, so that every cross-section parallel to the plane of the bend is the same curve, and every cross-section perpendicular to the plane of the bend is a rectangle. This is a first type of corner turner (In spite of the name "2D," it is a 3 dimensional object). The upper and lower surfaces of 2D corner turners are planar reflectors. A familiar example of this type of shape, which in the language of solid geometry may be called a "generalized right cylinder," is a curved 90 degree bend in rectangular-cross-section air conditioning duct. 2D corner turners are especially well-adapted for use with input and output optical beams having rectangular cross sections, although at some cost in dilution (see definition below) they may be used with input and output beams of circular or other cross sections.

3D corner turners may in general have differently-shaped curves in each cross section in the plane of the bend, and in each cross section perpendicular to that plane. This is a second type of corner turner. Their input and output cross sections may be adapted to the shape of associated input and output optics, which will in many cases be circular. A familiar shape of the general class to which 3D corner turners belong is a right-angle bend in round copper water tubing.

An article by Collares-Pereira et al., entitled "Redirecting Concentrated Radiation," Proc. SPIE, vol. 2538, pp. 131–135 (August 1995), describes a toroidal corner turner. This 3D device is thought by the present inventor to be the only previous published example of non-imaging optics for corner turning. The corner turner described, by its nature, is restricted to working efficiently with input and output beams, each of which has a maximum ray propagation angle of 90 degrees with respect to the beam axis (in air this corresponds to NA=1.0). If the input beam has less than a 90 degree divergence, the output beam may still have a 90 degree divergence. As such, this use of the toroid is ineffi-cient, which is to say that it does not minimize étendue of the output beam (étendue is defined, in the 2D case, as the product of NA and the beam diameter). In an application in which a toroidal corner turner was used to direct light from one optical fiber to another, both fibers having NA=0.5, much of the light entering the second fiber would be at angles exceeding NA=0.5, and would therefore quickly be lost as it propagated down the length of the second fiber.

Consequently, a device is needed which conserves éten-due while redirecting light around a corner that does not use imaging optics and can work efficiently with smaller input divergence than 90 degrees.

SUMMARY OF THE INVENTION

The present invention provides a device and method to efficiently turn light from an optical fiber around a corner that would cause excessive light loss, by failure of TIR, if the fiber were bent. The invention uses non-imaging optics which efficiently deal with divergence half-angles less than 90°. By recognizing that most light from a fiber optic source will have a divergence half-angle of less than 90 degrees, a practical solution is achieved using non-imaging optics.

A key point in all of the novel designs described herein is that, in their 2D forms, they avoid dilution of optical energy in phase space, which is to say that (to the extent that reflecting surfaces approach perfect specularity), the étendue of the beam leaving the corner turner does not exceed that of the entering beam, and all of the power of the input beam is delivered to the output beam. The word "dilution" has previously been used at least in H. Ries et al, "Consequences of skewness conservation for rotationally symmetric non-imaging devices," Proc. SPIE vol. 3139, pp. 47–58, 1997.

In one embodiment, an air or solid filled optical corner turner, for rays having a divergence half-angle of 60 degrees or less, is constructed for a 90 degree bend. A planar reflector is positioned angularly to the axial direction of the input channel on the inside of the turn. The length of this reflector is just long enough so that a ray entering the outside edge of the output channel at the maximum angle (60 degrees) is emitted by the input channel at its inside edge. Additionally, a reflector shaped as one segment of a parabola is con-structed extending from the input channel and another segment of a parabola is constructed extending from the output channel. To connect the two parabolic sections, an ellipse is constructed which meets both in such a way that the slopes of ellipse and parabola are equal at the point of contact.

The first embodiment works most effectively when the corner-turning angle is less than twice the maximum angle of rays with respect to the input and output optical axes. For example, in an air-coupled system having 0.5 NA input and output channels (30 degree maximum ray angle), the angle of corner turning should be less than 60 degrees. A second embodiment achieves larger corner turning angles by employing two or more first embodiment corner turners in series. For example, to achieve a 90 degree corner turner, a second-embodiment design is shown which uses two first embodiment corner turners connected together, each turning 45 degrees.

Where less than a 90 degree corner is required (such as for illuminating a tooth, perhaps), another embodiment uses a Compound Parabolic Concentrator (CPC) connected to a circular reflector at the outside of the turn. CPCs are well known, and have been described in various publications, including Welford and Winston, op. cit., but this combina-tion of a CPC with a circular reflector is novel.

Another embodiment provides a 90 degree corner turner for use with input and output channels having maximum ray angles of 90 degrees (NA=1 in an air-coupled system). A reflector is formed as ellipses on the inside and outside walls of the turn around the corner. The foci of the ellipses are the opposite connection points to the incoming and outgoing fiber optics.

Another embodiment is an alternate approach to the two 45 degree corner turners for a small numerical aperture, and may be made smaller. A CPC is used to convert incoming light from a small NA to a large NA. A large NA 90 degree corner turner (e.g., the two ellipses embodiment) can then be used. A second CPC is then used to transform the light from the large NA to the required small NA.

In an alternate embodiment, two CPCs can be used, with an elliptical reflector on the inside turn of the corner, and another elliptical segment reflector on the outside turn. Alternately, the inside turn could be eliminated by joining one edge of the incoming fiber optic to an edge of the outgoing fiber optic.

In one application, a first corner turner is used to direct light to a patient, such as for pulse oximetry. The first corner turner receives light of a small NA from the fiber optic. A second corner turner is used to provide transmitted light from the patient to a return fiber optic, and receives large NA input light and provides it to the smaller NA return fiber optic.

For a fuller understanding of the nature and advantages of the invention, reference should be made to the ensuing detailed description taken in conjunction with the accompanying drawings.

DESCRIPTION OF THE DETAILED EMBODIMENTS

I. Set-Up of the Problem

Figure 1:
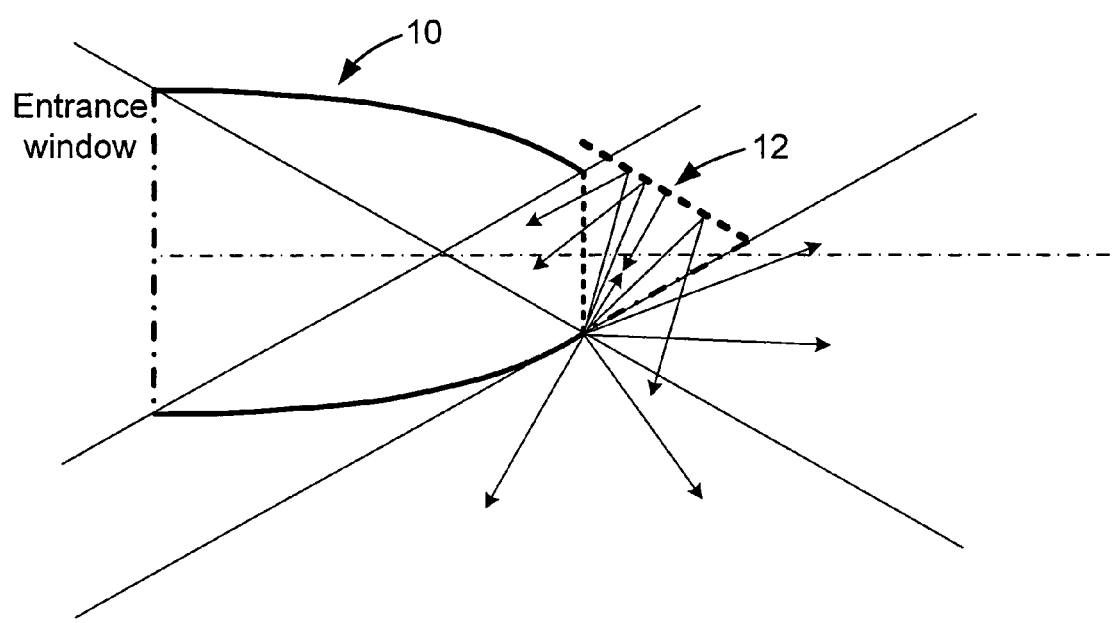
FIG. 1 is a diagram of the cross-section of a flat reflector attempting to redirect the output of a compound parabolic concentrator (CPC)

FIG. 1 shows an air-filled, two-dimensional, compound parabolic concentrator (2D CPC) 10, designed to accept rays at up to 30 degrees from the system axis (i.e., NA=0.5). As used herein, ϕ is defined as the maximum angle which a propagating ray may bear to the optical axis of input and output channels, θ is defined as the angle through which the corner turner rotates the optical axis, and the Numerical Aperture (NA) is defined as product of the sin of ϕ and the refractive index, n, of the medium in which light propagates. The examples presented herein are worked out for a medium with n=1 (i.e. air). For cases in which the medium of propagation has higher refractive index, e.g. for corner turners molded of solid plastic or glass, it is straightforward to calculate the appropriate value of ϕ if the NA of propagating light is known, as it commonly will be in the design of an optical system. At the exit surface of the CPC of FIG. 1, the rays have been concentrated into a region half the height of the input, but with a numerical aperture of 1.0. This is the maximum concentration allowed by conservation of étendue, which is a manifestation of the second law of thermodynamics. Conservation of étendue requires that the product of NA and system diameter be unchanged in an efficient optical system. If the product decreases, light must be lost from the system. If étendue increases, the concentration of light (brightness) is unnecessarily reduced (this is the process described above as dilution).

To the right of the CPC is a flat reflector 12, placed there in a misguided effort to rotate the output of the CPC so that it will go through a window turned at an angle to the main output window. FIG. 1 examines just the fan of rays leaving the lower corner of the CPC exit window. It can be seen that some of the rays are reflected back into the CPC, rather than emerging through the exit window. What is needed is a reflector design to redirect the entire output of the CPC to an output window.

II. A Solution to the Problem

To illustrate the design of a corner turner according to the first embodiment, a two-dimensional CPC for a particular set of design requirements is illustrated. The design of the CPC follows the method of Welford and Winston, op. cit., at pp. 55 ff. Thereafter, the design of a corner turner will be shown to work at the output end of this particular CPC. The construction of this CPC appears in FIG. 1A. The 2 mm height of the input surface, RS, is selected to accept the output of a 2 mm diameter plastic fiber with NA=0.5. The CPC is designed to squeeze all of the light in the fiber down into a minimal height so that, for example, it may be delivered to a region of a tooth just below the edge of a full crown (FIG. 1D).

Lines a and b are the limiting rays that enter the system in a downward-tilting direction, and lines c and d are the limiting rays in an upward-tilting direction. The height of the exit surface, TU, is calculated by conservation of étendue. Since the product of surface length and NA is conserved, and since we desire maximal concentration (which implies NA=1 at the output), the height of output surface TU must be 1 mm. Construction lines k and n are drawn in recognition of this fact—the output surface will lie between these lines. Line m, halfway between lines k and n, is the axis of symmetry of the system.

We find point U as the intersection of limiting ray a with construction line n. It has been proven algebraically by Welford and Winston that length VW of the CPC is given by:

$$VW = (TU/2)(1 + \sin \phi) \cos \phi / \sin^2 \phi,$$

where $\phi$ is the angle between the extreme entering rays and the system axis. Given, for example, that TU=1 mm and $\phi$=30° we have VW=2.6 mm.

The upper surface of the concentrator is constructed as a parabola with its focus at point U (the lower corner of the exit surface). The parabola must have its axis of symmetry parallel to limiting ray d. With these rules of construction, all rays parallel to limiting rays c and d will be reflected into point U, and all rays which enter the CPC at smaller angles will strike output surface TU at points above U.

The above shows how upper segment RT is constructed. The lower segment, curve g, is constructed in the same manner by symmetry. To the extent that the walls of the CPC are perfectly specularly reflecting, every point of the exit surface TU will emit rays over the full range of angles ±90° from horizontal. To have a smaller output window, it would be required by the second law of thermodynamics to use a smaller input window or to waste light.

Figure 1A:
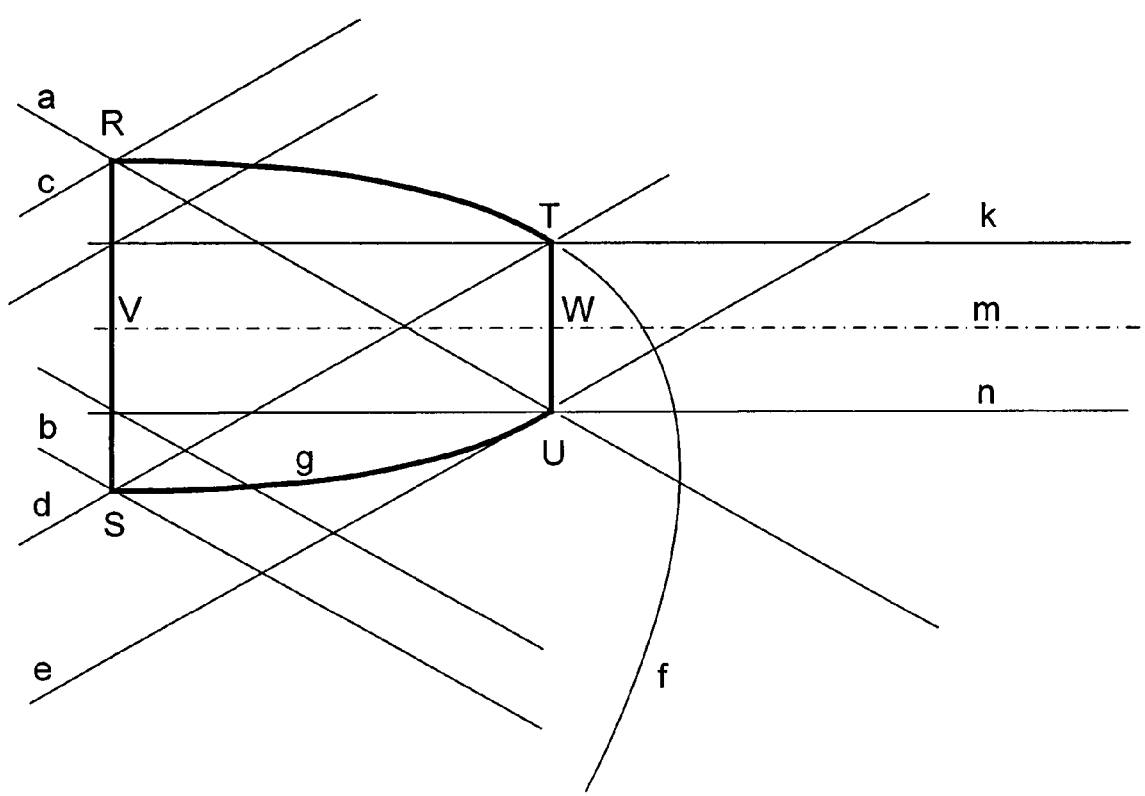
FIG. 1A is a diagram illustrating the construction of a maximally-concentrating 2D CPC with input 2 mm high at 0.5 NA.
Figure 1B:
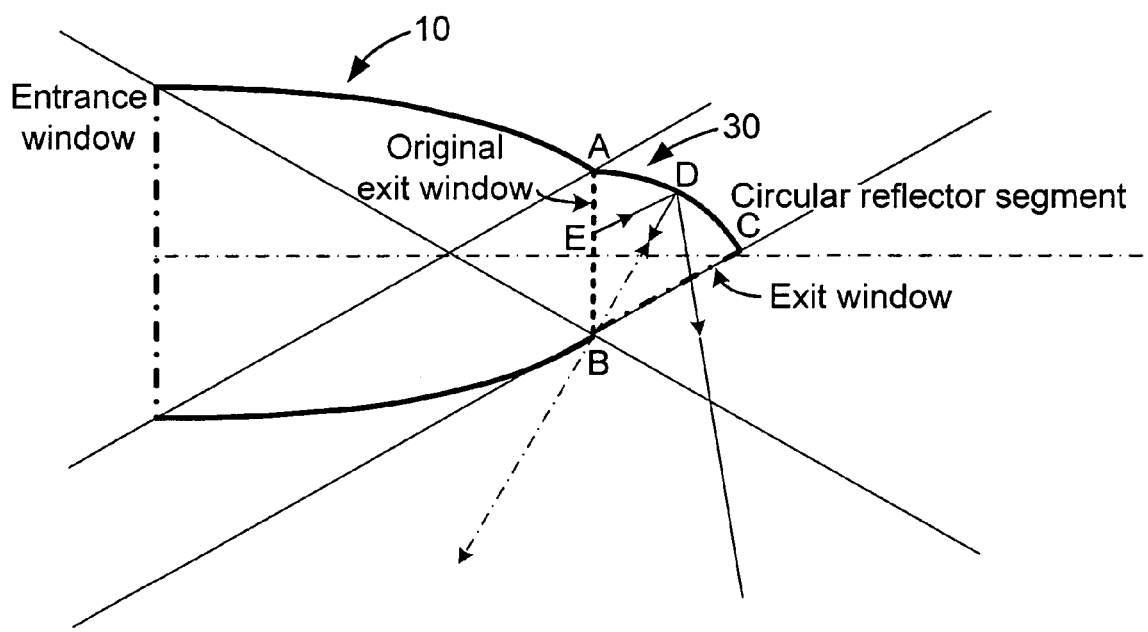
FIG. 1B is a diagram illustrating a circular mirror segment rotating the direction of light coming from the output window of the CPC.

A coincidence in the construction of FIG. 1A is that line e, as well as being the axis of parabola f, is the tangent to parabola g at exit point U. In general, the slope of the surface at point U will always be such as to reflect the limiting ray into vertical segment UT, so that the limiting ray strikes point T. In FIG. 1B, we will use line e's property of being the tangent to curve g. With some other limiting NA at the entrance, we would still use the tangent line, not the axis of parabola f. It can be shown that the angle between tangent line e and line segment TU is given by $\theta = (90° + \phi)/2$, which in this example equals 60 degrees.

2D Partial Corner Turn Embodiment for NA=1

FIG. 1B shows the addition of a reflecting surface of circular profile to rotate the output of the CPC without loss of power or brightness. Exit surface BC is of the same length as original exit surface AB (which is necessary if the brightness is to be maintained). Exit surface BC is rotated by $\theta$=60 degrees from original exit surface AB. The circular segment AC is centered on exit point B, and is of radius AB. The limiting line, in which exit surface BC lies, and which establishes point C at the end of the circular segment, is line e, tangent to the parabolic reflector. The reason for this limit is that rays leaving surface BC over a full 180° range would not otherwise be able to miss the wall of the CPC.

Figure 1C:
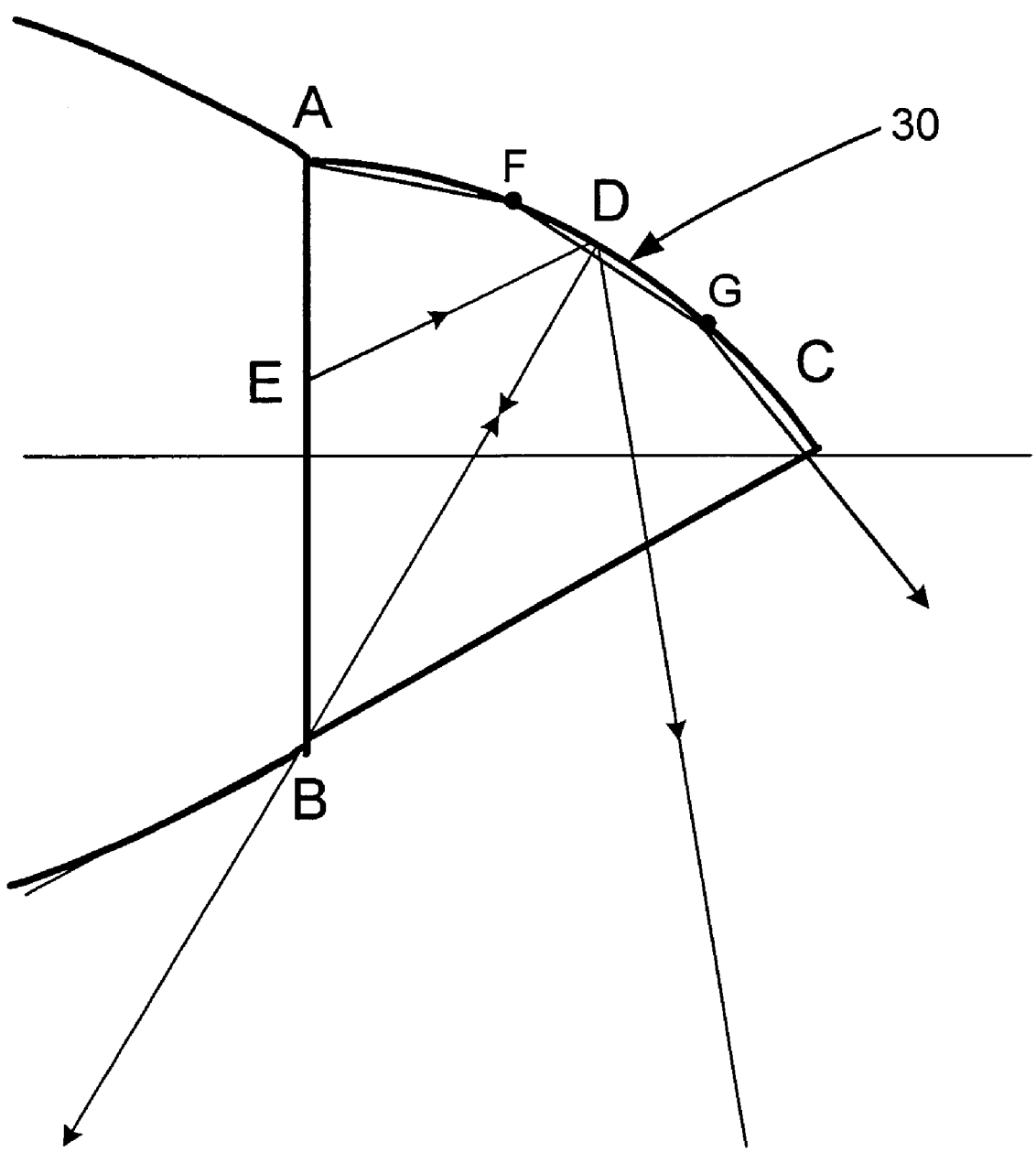
FIG. 1C is a diagram illustrating ray ED leaving the exit window on a single bounce. The shallow-angle ray from A requires two bounces at points F and G.
Figure 1D:
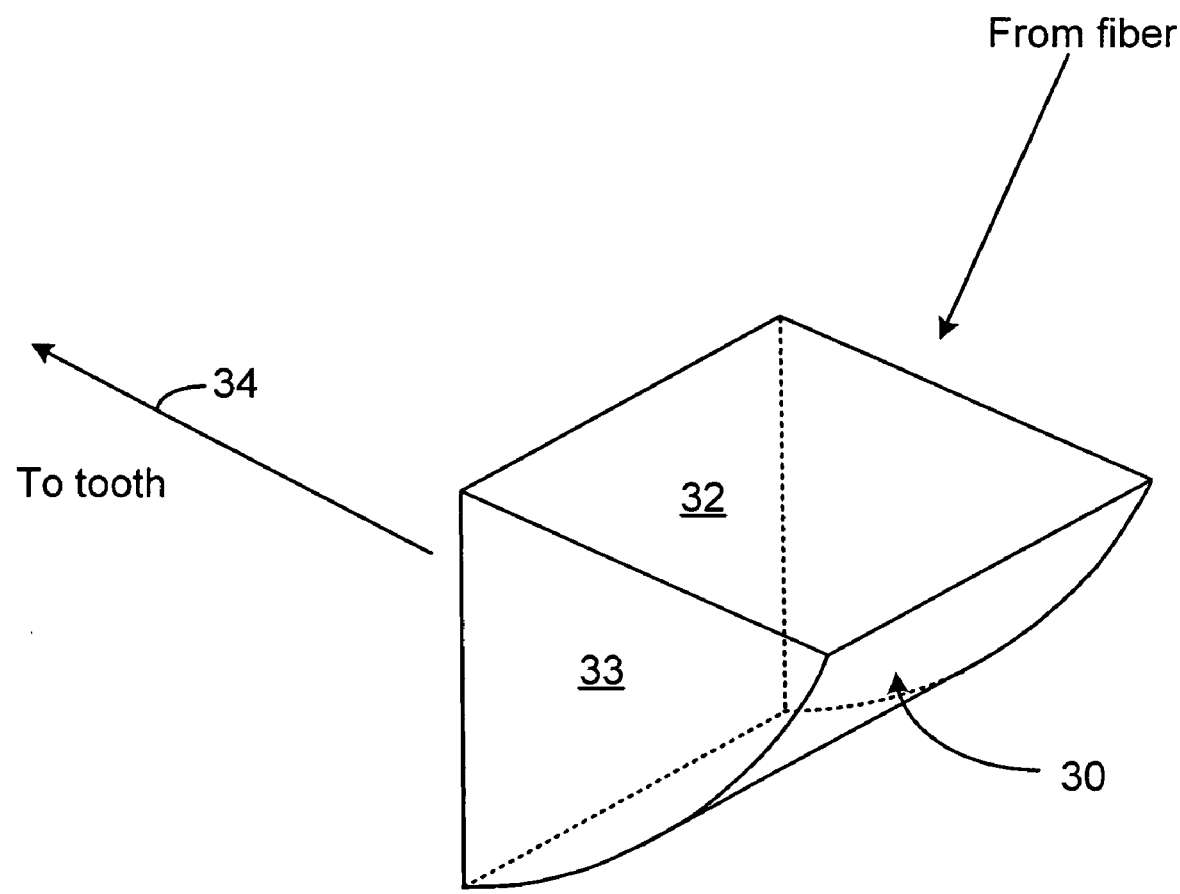
FIG. 1D is a diagram illustrating a 3D view of a possible application of the example device to the task of delivering light to a tooth (in the notation described above, this is a three-dimensional view of a "2D" corner, which is to say that every cross section in the plane of the bend is the same)

FIG. 1C is a larger view of FIG. 1B showing ray ED leaving the exit window on a single bounce. Additionally, a shallow-angle ray from point A is shown requiring two bounces, one at point F and one at point G. Rays which strike surface AC at still shallower angles may require still more bounces to exit, but in principle every ray which passes through surface AB will eventually exit through surface BC.

FIG. 1D is an example of how this invention might be applied to deliver light from an optical fiber to a tooth. The circular portion 30 of the embodiment of FIGS. 1B and 1C (excluding the CPC) is shown, extended into 3 dimensions by moving curve AC perpendicular to its own plane. The reflective structure is closed by planar reflecting surfaces, of which one is visible at 33. A 1 mm×2 mm rectangular input surface 32 would connect to the fiber optic (which could be rectangular or circular), with up to 0.5 NA. The exiting light 34 is directed to the tooth.

It will be clear to one skilled in optical design that the method illustrated in this example may be used to design an efficient 2D corner turner for any turning angle up to $\theta = (90° + \phi)/2$, for any value of maximum input ray angle $\phi$. The same design method may in fact be used for larger turning angles, with the consequence that some of the exiting rays will strike the outside surface of the CPC, unless they are captured by an additional optical component.

2D 90 Degree Turn Embodiment for NA=1 (Two Ellipses)

Figure 1E:
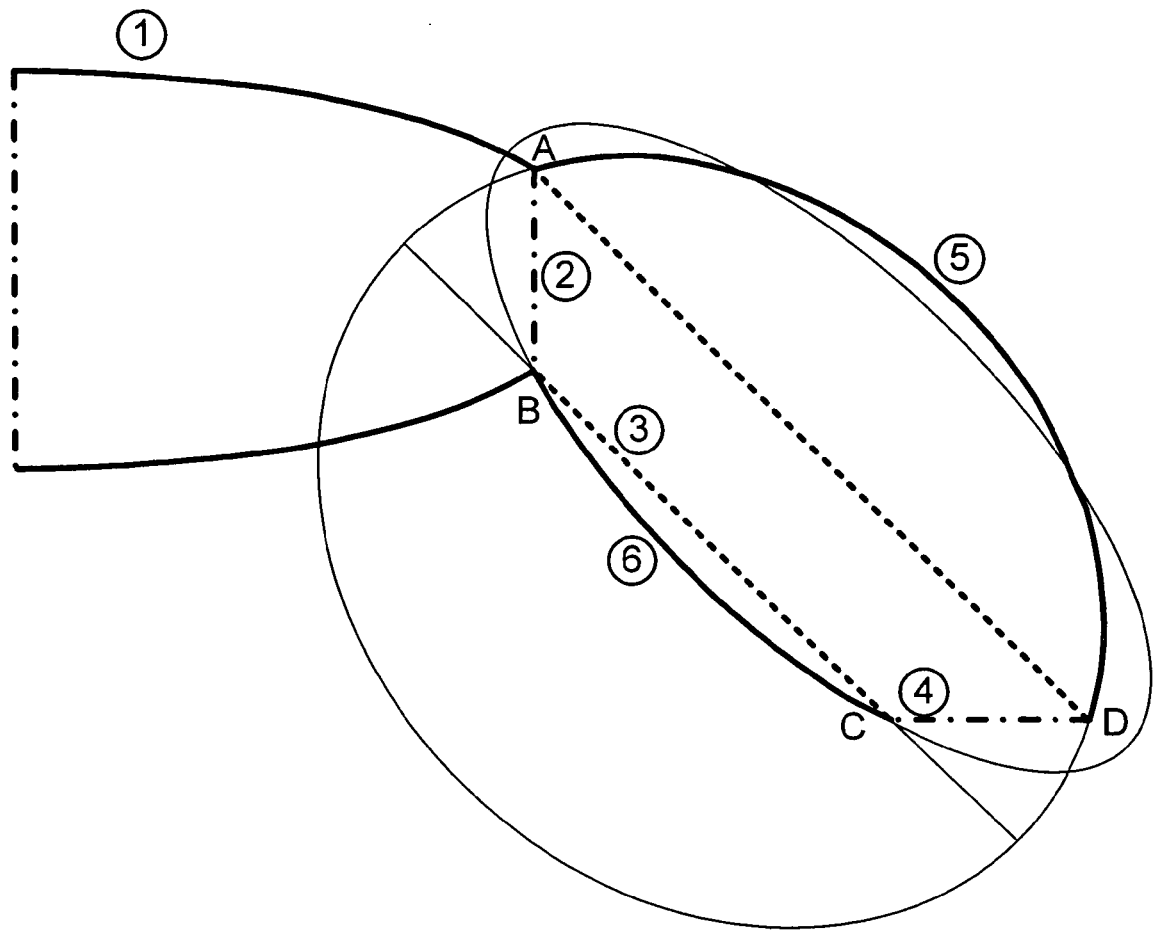
FIG. 1E is a diagram showing the construction of a generalized 2D corner turner with NA=1.

FIG. 1E shows a method of designing a reflector according to this invention. The input portion of the reflector, labeled (1), is a Compound Parabolic Concentrator (CPC) with input NA=0.5, as described above. The output plane of the CPC, labeled (2), is a plane 1 mm long, at which NA=1. It would be possible to construct an appropriate CPC, using known methods, so that whatever the input NA, the output would have NA=1 and the output plane would be reduced in scale by the same ratio that the input NA was increased. This is, for air-coupled systems, the greatest concentration permitted by the second law of thermodynamics, which appears in optics as conservation of étendue.

Since we want to turn the output of the CPC through an angle $\phi$, we start by constructing a line beginning at the lower output corner, B, of the CPC, at an angle of $\phi/2$ below the normal to the CPC output. In the illustration, $\phi$=90° and line (3) is constructed at 45°. A useful feature of the method is that this line may be of any desired length (i.e., the corner-turner output may be as far as desired from the CPC exit). In this particular case, the length has been chosen arbitrarily to be 2.5 mm.

The exit window, labeled (4), is now constructed at the end of line (3). Consistent with the perfect efficiency of well-designed non-imaging optics, the length of the exit window is the same as the length of window (2) so that the intensity will be unchanged.

Next, we construct an ellipse passing through the upper ends, A and D, of the two windows and having the lower ends, B and C, as foci. The section of the ellipse between points A and D (5) becomes the upper reflecting surface of the corner turner. The lower reflecting window of the corner turner is segment (6) of a different ellipse which has A and D as foci and which passes through B and C.

Figure 1F:
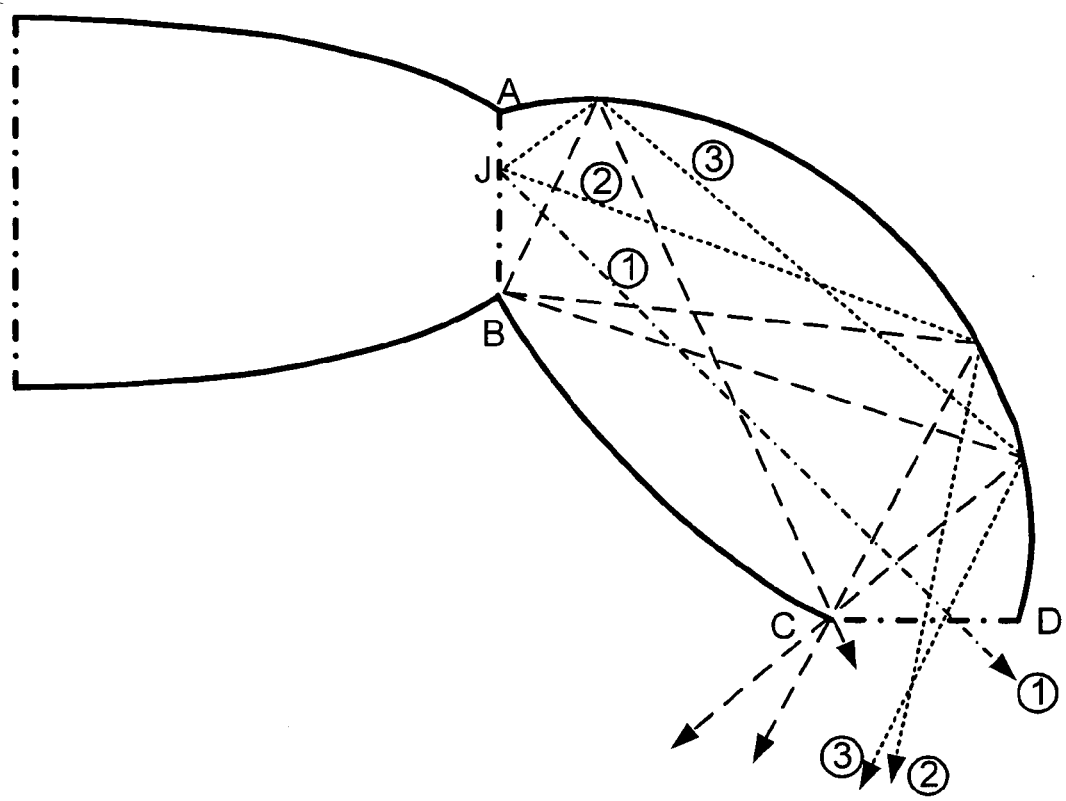
FIG. 1F is a diagram demonstrating that all rays entering the corner turner will emerge at the exit.

FIG. 1F illustrates the corner-turner's ability to transfer all rays from input to output. A ray leaving a general point J on the window AB will either emerge directly through window CD (e.g. ray (1)) or it will strike one of the ellipses. In the latter case, the ray from J must reflect at an angle further from the normal than the ray from B so that it must either reach exit window CD (as does ray (2)) or again strike the upper ellipse (as does ray (3)). The ray from J will eventually find its way to window CD.

Figure 1G:
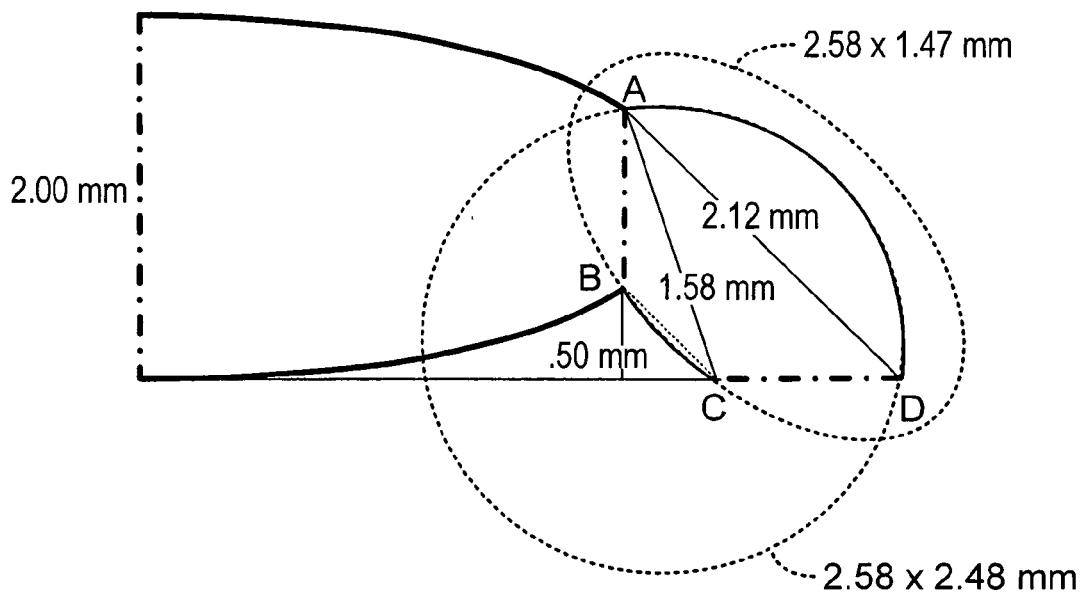
FIG. 1G is a diagram illustrating the smallest 90 degree corner turner that clears the incoming CPC.

A particularly interesting variant on the above design is a 90° corner turner that is as small as possible while still permitting all rays to clear the outside of the CPC that feeds light into the device. FIG. 1G shows such a device where ideally the reflectors making up the CPC are of zero thickness.

Figure 1H:
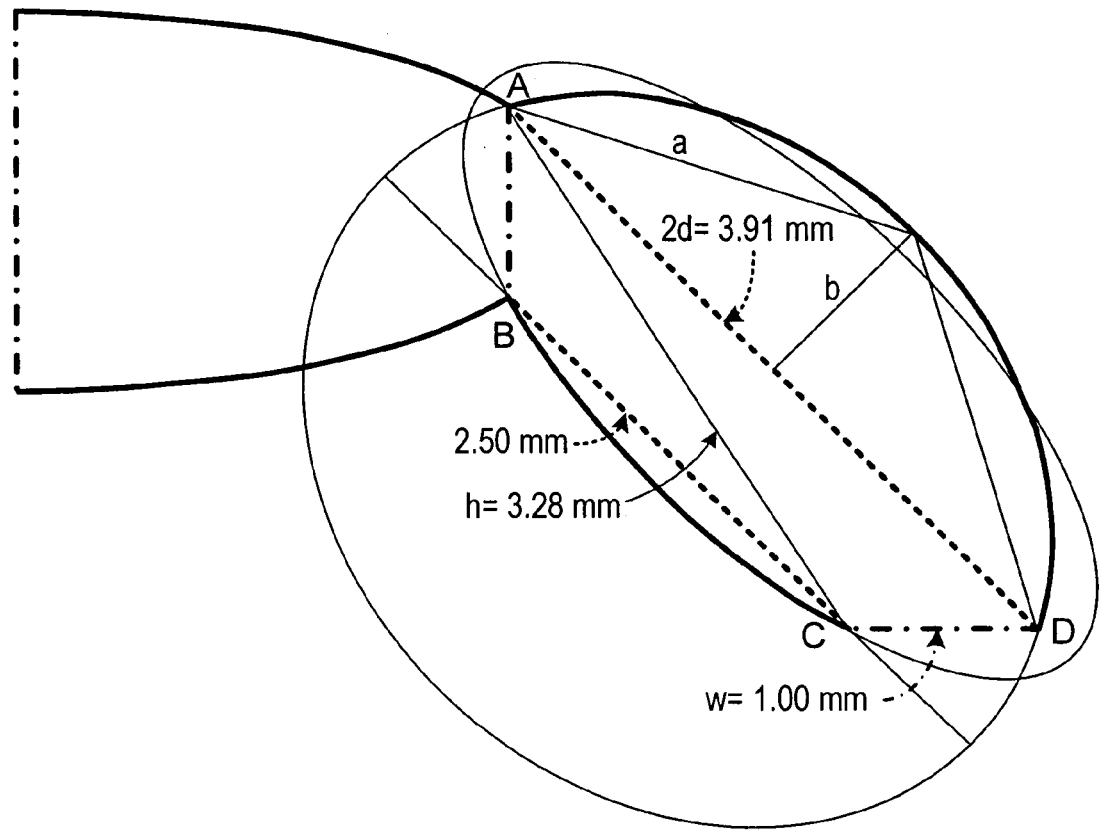
FIG. 1H is a diagram showing how the upper ellipse is constructed.

In FIG. 1H, we demonstrate the general principles of construction used in setting up the elliptical reflective walls. FIG. 1H has been labeled to support a demonstration of the calculations for the lower elliptical segment, BC. This is an ellipse with foci A and D. The steps are as follows:

The spacing between foci, which is called 2d, is calculated by trigonometry. In this particular case, 2d is the hypotenuse of a 45° right triangle whose side is $(1+2.5/\sqrt{2})$, so $2d=\sqrt{2}+2.5=3.914$ mm.

The slant distance from focus A to the opposite contact point, C, can be calculated by trigonometry as $h=\sqrt{[w^2+(2d)^2-2w(2d)\cos 45°]}=3.284$ mm.

The sum of distances from any point on an ellipse to the two foci is 2a, the length of the major axis. We can therefore compute $2a=w+h=4.284$ mm.

The minor axis of the ellipse can be computed as the side of a right triangle, $b=\sqrt{(a^2-d^2)}=0.871$ mm.

We therefore create an ellipse with major axis $2a=4.284$ mm and minor axis $2b=1.742$ mm, and center it with respect to foci A and D.

A similar calculation for the upper elliptical segment goes as follows:

Distance between foci $2d=2.5$ mm by postulate.

Slant distance from one focus to opposite contact point $h=\sqrt{[(AB)^2+(BC)^2-2(AB)(BC)\cos 135°]}=3.284$ mm (this calculation gives the same result as the similar calculation for the upper ellipse).

Major axis $2a=1+3.284=4.284$ mm (so the two ellipses have identical major axis lengths).

Half-minor axis $b=\sqrt{(a^2-d^2)}=1.739$ mm (different from the other ellipse, because the distance between foci is shorter).

We therefore draw an ellipse centered on foci B and C, with major axis $2a=4.284$ mm and minor axis $2b=3.478$ mm.

It will be understood by skilled optical designers that the method illustrated here may be employed to design 2D corner turners for any turning angle θ, for any desired length of line BC, and (by appropriately designing the input CPC) for any maximum input ray angle φ.

For both this design and the one previously described (the "partial corner turn embodiment"), it is not required that the input stage be a CPC. Other known optical designs, such as the "trumpet concentrator", may be used to produce the 90 degree maximum ray angle at plane AB for which this type of design is optimized. Furthermore, in applications in which conservation of étendue is not required and in which it is not required that the maximum angle of output rays match the maximum angle of input rays, these corner turners may be used with optical input at plane AB having maximum ray angle less than 90 degrees. One family of such applications is the use of fiber optics with corner turners to apply light to living tissue. Because of the strong scattering that light typically undergoes in tissue, the exact distribution of input angles is often not very important-after a relatively short propagation distance in the tissue, the propagation direction of photons will be essentially random, no matter what the input angular distribution.

It will be understood by those skilled in optical design that the concentration of rays exhibited by the 2D concentrators thus far described occurs only in the plane of the bend. For example, if rays enter these optical systems with maximum angles of 30°, they will emerge with maximum angles of 90° in the plane of the bend, but still 30° in the perpendicular plane.

2D Corner Turner with Flat Inside of Turn Reflector, and Parabolic-Elliptical-Parabolic Outside of Turn Reflector A group of embodiments will now be described which relax the requirement that rays entering the corner turner be concentrated to obtain φ=90° in the plane of the bend at the input of the corner turner. It is convenient to break this limited-NA problem into several cases. Defining φ as the maximum angle which a propagating ray may bear to the optical axis of input and output channels, and φ as the angle through which the corner turner rotates the optical axis, the three cases are: Large NA: φ>θ/2; Medium NA: φ=θ/2; and Small NA: φ<θ/2. The corner turner used for the large NA (φ>θ/2) case is different from those used for the other cases. The large-NA corner turner often has the desirable property of being very compact. Different designs were needed for the small and medium NA cases, because in these cases the large-NA design cannot limit the NA of output rays to equal the NA of input rays.

1. The Large NA Case (φ>θ/2)

Figure 1I:
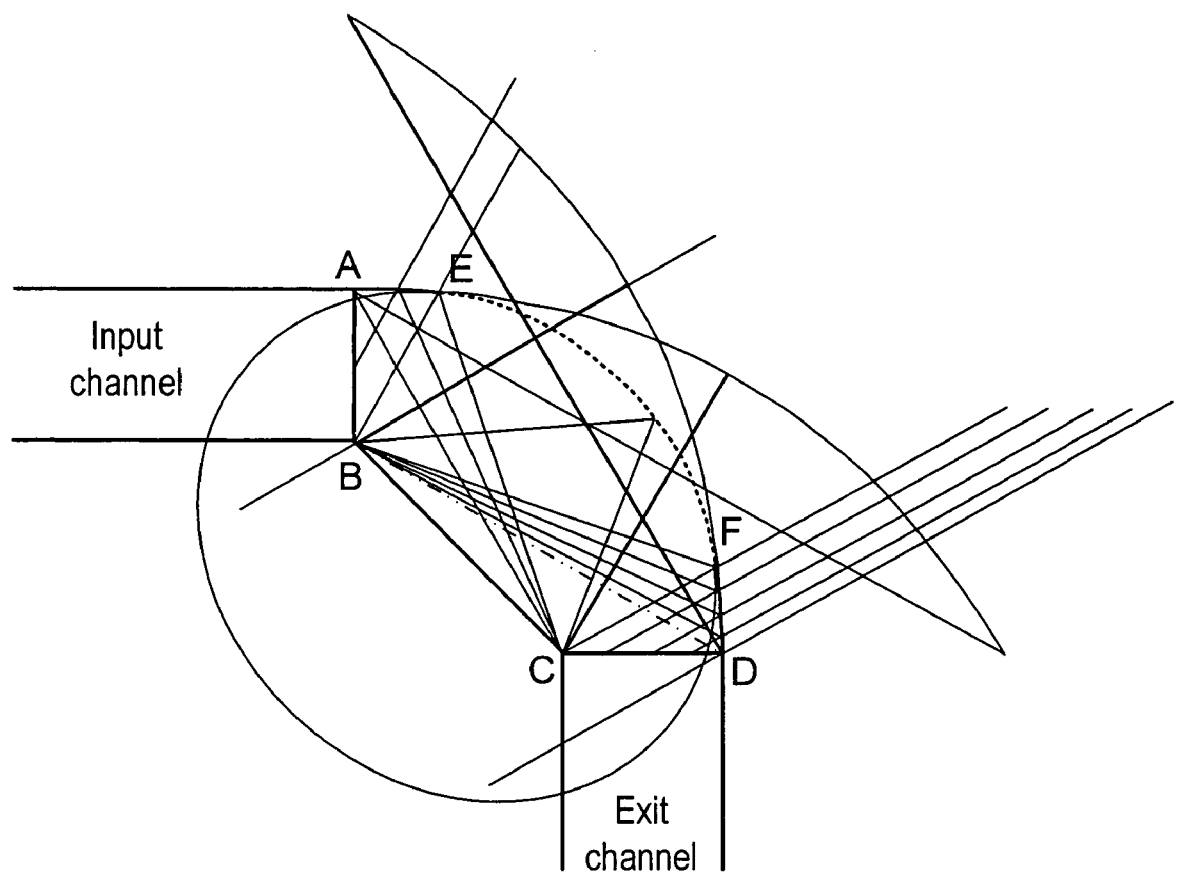
FIG. 1I is a diagram illustrating a 90 degree corner turner with ϕ=60 degrees.

FIG. 1I shows a finished design for the case where θ=90° and φ=60°. This class of device may become inconveniently large when φ is close to θ/2. If that happens, it could be appropriate to use one of the methods shown for the small-NA case. The input channels are either circular or rectangular in cross-section. For most-efficient use of this 2D design, both input and output channels will be rectangular. The entrance window of the corner turner (line AB) has the same width, here scaled to be 1 mm, as does exit window CD. The reflective surface components of the corner turner are as follows:

Line BC is a planar (straight) reflector, rotated below the axial direction of the input channel by angle θ/2 (45° in this example). The length of this reflector is just sufficient so that ray BD is at the extreme acceptable angle for rays going into the exit channel (i.e., 60° from the normal to CD).

Curve DF is a segment of a parabola with focus at B, whose axis is turned at the extreme acceptable angle for rays going into the exit channel (i.e., 60° from the normal to CD). Curve DF extends from corner D of the exit channel (i.e., 60° from the normal CD). Curve DF extends from corner D of the exit channel just far enough to catch the extreme-angle ray from corner C. The parabolic segment blends smoothly into the wall of the exit channel (their slopes match at the point of contact).

Curve AE is a segment of another parabola constructed symmetrically to DF.

Curve EF is a segment of an ellipse, passing through points E and F and having points B and C as foci. The ellipse blends smoothly into the two parabolic segments (they have the same slopes at the points of intersection).

Figure 1J:
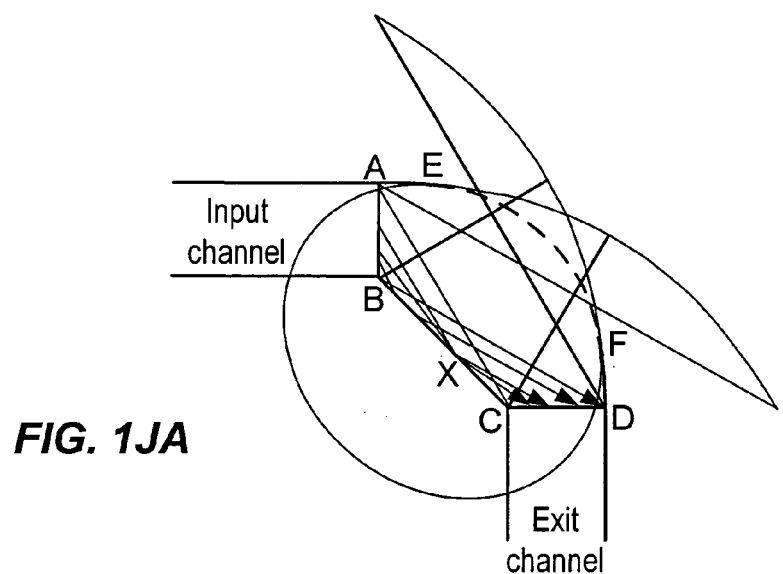
FIG. 1J is a diagram showing the tracings of several categories of rays (A–E)
Figure 1J:
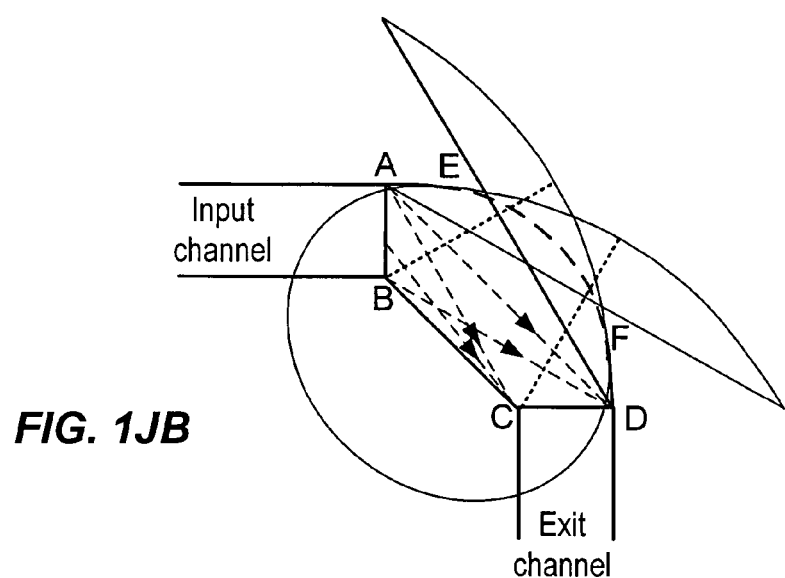
Figure 1J:
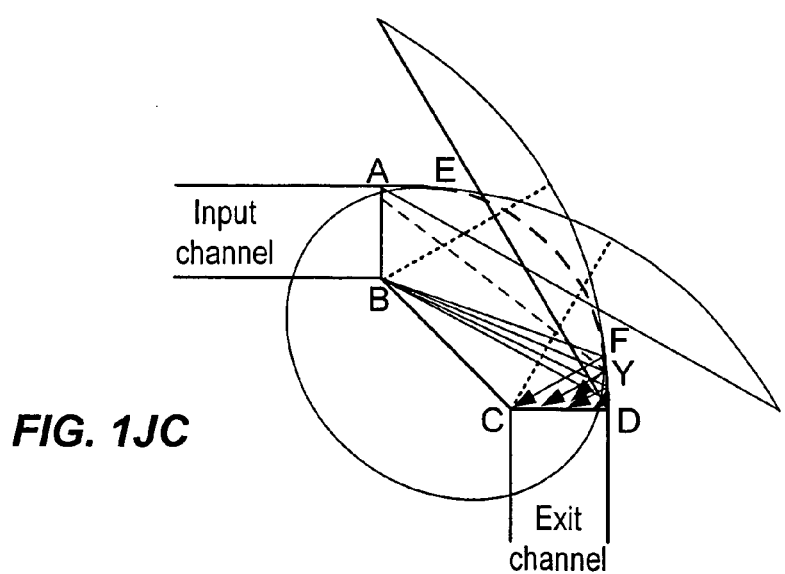
Figure 1J:
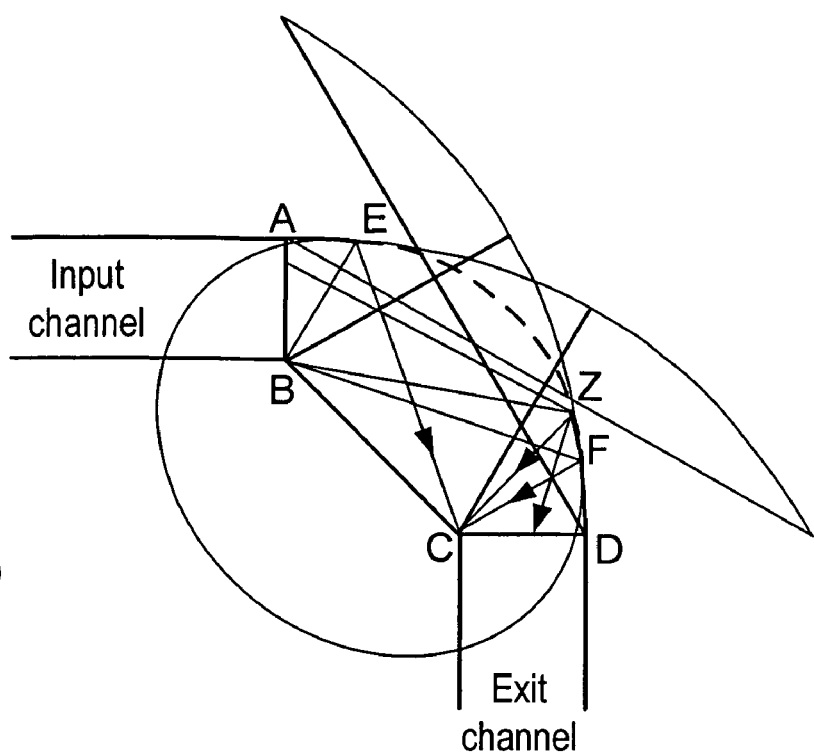
Figure 1J:
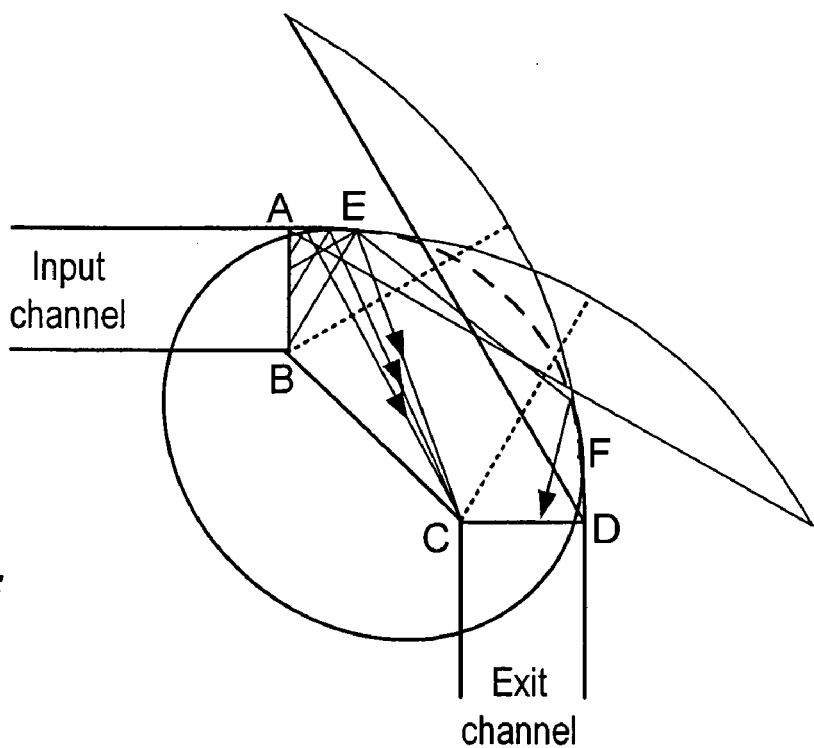

In FIG. 1J, we examine the fate of rays from the entrance aperture that strike different reflective segments. The goal of this examination is to show that all such rays strike the exit aperture, and do so at angles not exceeding φ. FIG. 1JA shows a parallel set of rays which leave entrance surface AB at the extreme permitted angle, φ. By symmetry, these rays reflect onto exit surface CD. The length of segment BC is chosen so that these rays do in fact exactly fill CD. Also shown is one additional ray which strikes a point X on the reflector at an angle shallower than the extreme rays (no steeper angles are possible because rays at angles exceeding φ do not propagate in the input channel). The test ray reflected at X must strike exit surface CD to the left of the reflected extreme ray and at an angle less than φ. Thus, all rays which strike surface BC are captured.

FIG. 1JB shows several extreme rays which propagate directly from entrance to exit surface. Because line BD was laid out to be at the extreme acceptance angle of the exit window, none of the direct rays strike CD at an angle exceeding φ so that all of them are captured.

FIG. 1JC shows a fan of rays leaving point B, reflecting from the parabolic segment DF, and coming to surface CD at the permitted extreme angle φ. Also shown is a ray from a point above B which strikes point Y on the parabola. Because this ray strikes Y at an angle further from normal than does the extreme ray from B, it will be reflected so as to strike exit surface CD at an angle less than φ. Therefore, all such rays are captured.

FIG. 1JD shows three rays leaving point B which strike the elliptical segment EF and are focused at C. Also shown is one ray from another point on entrance surface AB which strikes point Z on the ellipse. Because it strikes at an angle above the ray BZ, it will reflect to a point on CD to the right of C (or conceivably it will strike a lower point on the ellipse, or on parabola DF, and "walk down" the surface until it strikes CD). In any event, all such rays are captured.

Finally, consider rays which leave surface AB in an upward direction and strike parabolic segment AE. This case is illustrated in FIG. 1JE. Rays leaving AB at the extreme available angle φ are focused at C, and rays leaving AB at angles closer to the normal will either strike CD to the right of C, or will strike somewhere along the compound curved surface and walk along the curve to CD. One such ray is illustrated.

In FIG. 2, the calculations required to create the shapes described in FIGS. 1I and 1J are shown. Methods of calculation adapted to general values of φ and θ are used rather than taking advantage of the special properties of 60° and 45° angles.

Figure 2A:
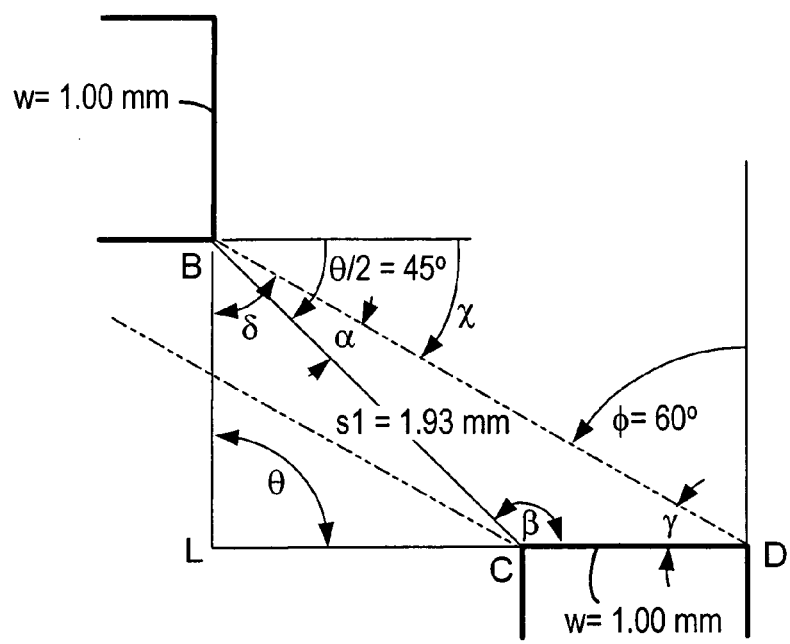
FIG. 2 is a diagram illustrating the construction steps of a corner turner (A–C)
FIG. 2D is a diagram showing the geometric constraint for the small-NA case if solution is to be single-step.

The first step, shown in FIG. 2A, is to construct the flat reflector BC. In order to achieve the necessary symmetry, this reflector is tilted at half the desired rotation angle for the output beam (in this example, θ/2=45°). The left edge of the exit window will touch this reflector. We then draw the envelope of extreme-angle rays which can be accepted by the exit window (dotted lines tilted at 60° from normal to CD). By making the extreme-angle ray from D pass through B, we ensure that no ray that passes directly from the entrance window to the exit window will strike exit window CD at any angle exceeding φ+60°. Thus, exit window CD will lie between two lines radiating from point B (its left edge on reflector BC and its right edge on line BD).

We next calculate the appropriate length of BC to make the length of exit window CD equal to the length of the entrance window AB. It is already known that line BC lies at θ/2=45° below the axis of the entrance channel. In order to find how far line BD lies below the axis, the internal angles of triangle BLD and angle χ are found first.

γ=(90°−φ)=(90°−60°)=30°.

δ=(180°−γ−θ)=(180°−90°+φ−θ)=(90°+φ−θ)=(90°+60°−90°)=60°

Therefore, χ=(90°−δ)=(90°−90°−φ+θ)=)θ−φ=30°.

Next, the internal angles of triangle BCD are calculated.

α=θ/2−χ=(θ/2−θ+φ)=45°−30°=15°.

γ=90°−φ=30°.

β=(180°−α−γ)=(180°+θ/2−φ−90°+φ)=(90°+θ/2)=135°.

Now the length of line BC=$S_1$ can be calculated (using the fact that, in any triangle, the ratio of each side to the sine of the opposite angle is the same for all sides):

$$\frac{s_1}{\sin\gamma} = \frac{w}{\sin\alpha} \quad [1]$$

$$s_1 = \frac{w\sin\gamma}{\sin\alpha} = \frac{1\sin 30°}{\sin 15°} = 1.93185 \quad [2]$$

Therefore, the exit window is drawn as a line 1 mm long, rotated by θ=90° from the entrance window, with its left edge C contacting the end of reflector BC.

Figure 2B:
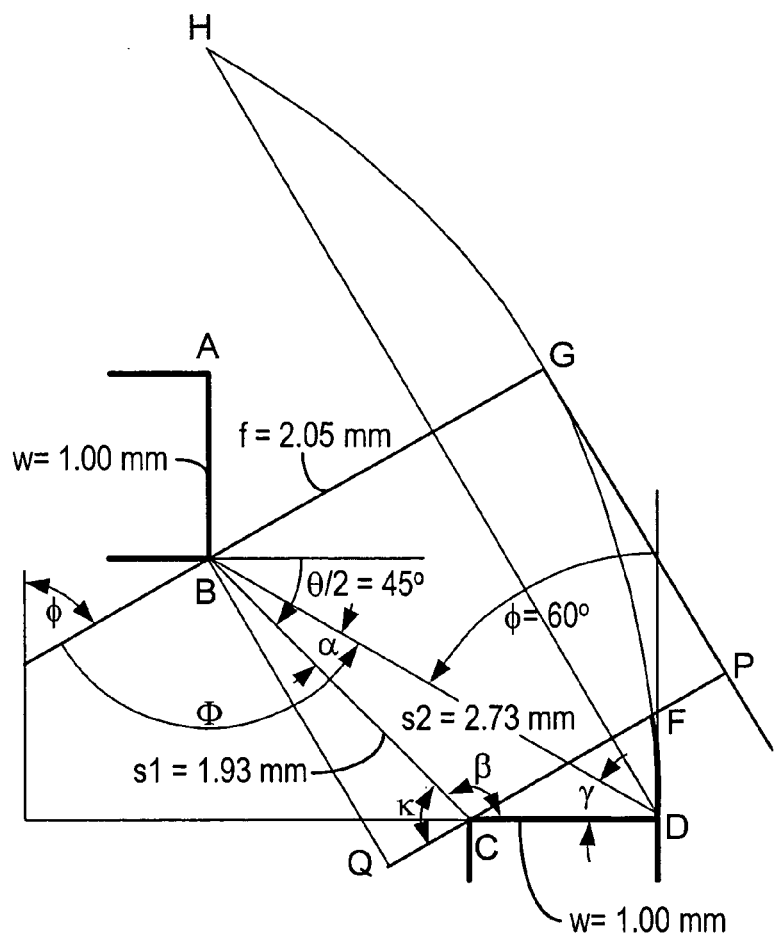

The next step, illustrated by FIG. 2B, is to construct the parabolic segment FD. By definition, the axis of the parabola passes through its focus, B, at an angle φ from the normal to exit window CD. The focal length of the parabola can be computed by representing the equation of a parabola in polar form. With the pole at the focus, the general formula is:

$$r = \frac{2f}{1-\cos\Phi}, \quad [3]$$

where r is the radius measured from the focal point, f is the focal length (distance from focal point to the base of the parabola), and φ is measured from the axis in the direction shown in FIG. 2B. Radius $S_2$ and angle φ are calculated first. Thereafter, focal length f is calculated.

Radius $s_2$ is calculated by the same method just used to get $s_1$.

$$\frac{s_2}{\sin\beta} = \frac{w}{\sin\alpha} \quad [4]$$

$$s_2 = \frac{w\sin\beta}{\sin\alpha} = \frac{1\sin(90°+\theta/2)}{\sin(\Phi-\theta/2)} = \frac{\sin 135°}{\sin 15°} = 2.732 \text{ mm} \quad [5]$$

Consequently:

Φ=2·φ=120°  [6]

So:

$$f = s_2\frac{(1-\cos\Phi)}{2} = 2.732 \text{ mm}\frac{1-\cos 120°}{2} = 2.049 \text{ mm} \quad [7]$$

The parabola is now fully specified. The length of the parabolic segment must be just great enough to catch all the extreme-angle rays from CD. Line CF is therefore constructed at angle φ from the normal to CD to delimit the parabolic segment.

Figure 2C:
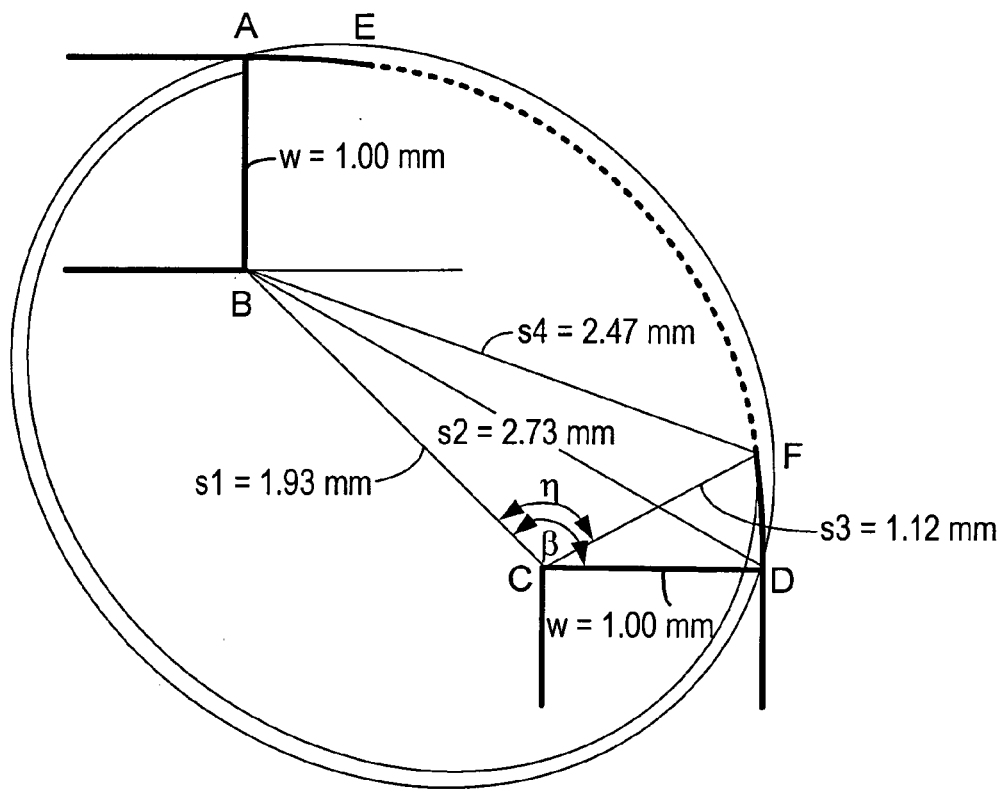

FIG. 2C shows how elliptical section EF, which has B and C as foci, is constructed. Also shown in FIG. 2C, for comparison, is elliptical section AD, which would have been constructed for the case having input NA of 1 (φ=90°). The strategy used previously for calculating the size of an ellipse is used to calculate the size of the ellipse through E and F. The added complication is that it takes extra work to find the length of line BF, which is the distance from one of the foci to one end of the elliptical segment. The strategy is as follows:

Find out where point F is in space.

Calculate the length of line CF (also called $s_3$ in the drawing) and angle η.

From the known values of s1, η, and $s_3$, calculate the length of line BF, also called $S_4$.

From $s_3$ and $s_4$, calculate a.

From a and d (which is half the distance between B and C), calculate b.

To locate point F, begin by observing (in FIG. 2B) that line CF is parallel to the axis of the parabola, BG. Both of these lines were constructed to be at the extreme acceptance angle of the exit window. Draw the perpendiculars GP and BQ, connecting BF with an extension of CF. These perpendiculars are of equal length. Angle κ can be calculated as:

$$\kappa=180°-\beta+(90°-\phi))=180°-(90°+\theta/2)+(90°-\phi)=180°-\theta/2-\phi=180°-45°-60°=75°.$$

Now line segments QC and BQ can be computed from:

$$QC=s_1 \cos \kappa=1.93185 \cos 75°=0.5 \text{ mm; and}$$

$$BQ=s_1 \sin \kappa=1.93185 \sin 75°=1.866 \text{ mm}.$$

Line segment PF can be computed by using one of the equations of a parabola. When the origin is at the vertex of the parabola, $y^2=4fx$.

So:

$$(PF)=(GP)^2/4f=(1.866)^2/(4\times 2.049)=0.424 \text{ mm}.$$

Now we can compute:

$$s_3=QP-QC-PF=f-0.5-0.4248=2.049-0.5-0.4248=1.1242 \text{ mm}$$

Calculate angle η:

$$\eta=\beta-(90°-\phi)=(90°+\theta/2)-(90°-\phi)=\theta/2+\phi=45°+60°=105°.$$

Finally:

$$s_4=(s_1^2+s_3^2-2s_1s_3 \cos \eta)^{0.5}=(1.93185^2+1.1242^2-2\cdot 1.93185\cdot 1.1242 \cos 105°)^{0.5}=2.474 \text{ mm}.$$

Since the sum of the distances from a point on an ellipse to the two foci is equal to the major axis length:

$$2a=s_3+s_4=1.124+2.474=3.598 \text{ mm, where}$$

a=1.799 mm

Using a right-triangle solution for b gives:

$$b=\left[a^2-\left(\frac{s_1}{2}\right)^2\right]^{0.5}=\left[1.799^2-\left(\frac{1.93185}{2}\right)^2\right]^{0.5}=1.518 \text{ mm} \quad [8]$$

so: 2b=3.035 mm.

So we construct an ellipse whose axes are 3.598 mm and 3.035 mm, tilted at 45° from the axis of the input channel and position it to intersect points E and F. This completes the construction of this particular embodiment of the reflector.

2. The Small NA Case ($\phi<\theta/2$) and Medium NA Case ($\phi=\theta/2$)

Figure 2D:
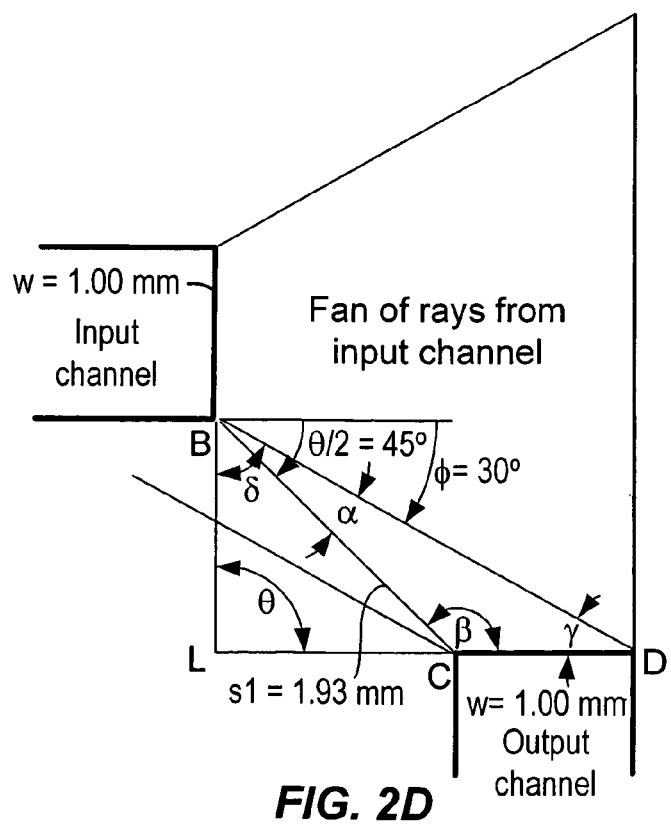

FIG. 2D shows what must be accomplished to have a single-step solution for the small NA case (the illustration is for $\phi=30°$, $\theta=90°$).

Ray BD, which is the lowest extreme ray from the input channel, must miss the output channel since this ray would enter the channel at an angle exceeding $\phi$ from the channel's optical axis. Symmetry in this setup places left corner C of the output channel on the 45° line BC and a desire for minimum system size puts the right corner D on 30° line BD. In order for the output channel to be any closer to the input channel, there would need to be some sort of barrier blocking direct ray BD. While there may be a simple set of reflective surfaces, analogous to those used in the large-NA case, that meet these constraints, it has appeared expedient to provide two alternative solutions, which follow.

a. The Small NA Case ($\phi<\theta/2$) and Medium NA Case ($\phi=\theta/2$)

(First Solution)

Figure 3A:
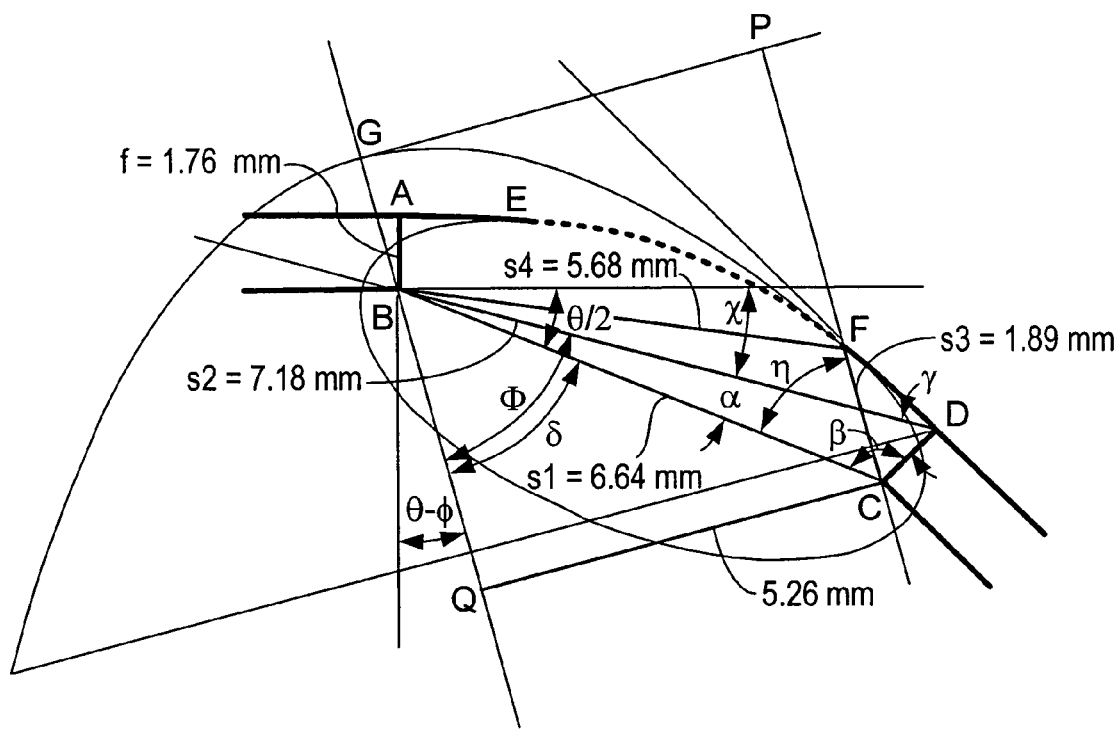
FIG. 3 is a diagram showing the construction of a non-imaging corner turner with ϕ=30 degrees and θ=90 degrees, by combining two 45 degree corner turners (A–C)
Figure 3B:
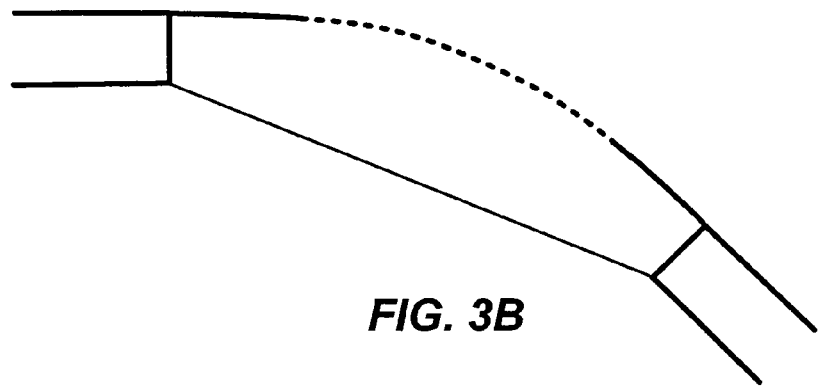
Figure 3C:
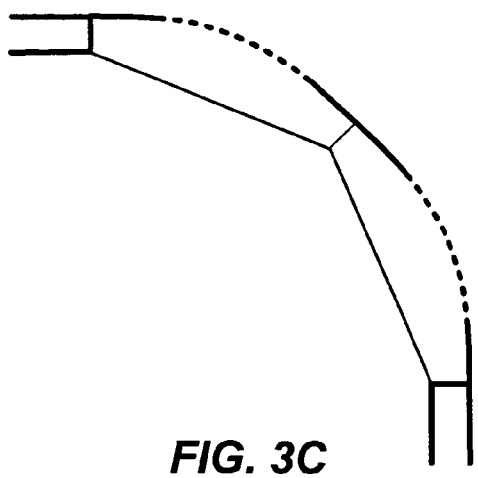

In an alternate embodiment, we divide the total turning angle, θ, into enough parts so that for each part the maximum ray acceptance angle, $\phi$, is greater than θ/2. This is illustrated in FIG. 3 with $\phi=30°$ and $\theta=90°$. FIG. 3A illustrates the particular angles and measurements for a 45 degree corner turner with $\phi=30$ degrees and $\theta=90$ degrees. Removing the construction line of FIG. 3A results in FIG. 3B. FIG. 3B is a 45 degree corner turner. To obtain a 90 degree corner turner, one simply connects two 45 degree corner turners together, as shown in FIG. 3C.

The calculation for this case follows the outline of the large-NA case. Using the same formulas:

$$\chi=\theta-\phi=45°-30°=15°$$

$$\alpha=\phi-\theta/2=30-22.5°=7.5°$$

$$\gamma=90-\phi=60°$$

$$\beta=90+\theta/2=112.5°$$

$$s_1=\frac{w \sin \gamma}{\sin \alpha}=1\cdot\frac{\sin 60°}{\sin 7.5°}=6.63488 \text{ mm} \quad [9]$$

$$s_2=w\frac{\sin\beta}{\sin\alpha}=1\cdot\frac{\sin 112.5°}{\sin 7.5°}=7.07812 \text{ mm} \quad [10]$$

$$\Phi=2\cdot\phi=60°$$

$$f=s_2\frac{1-\cos\phi}{2}=7.07812\cdot\frac{1-0.5}{2}=1.76953 \text{ mm} \quad [11]$$

$$\delta=90°-(\theta-\phi)-\theta/2=90°+\phi-3\theta/2=90°+30°-(1.5\cdot 45°)=52.5°$$

$$QC=s_1 \sin \delta=6.63488 \sin 52.5°=5.26380 \text{ mm}$$

$$PC=GQ=f+BQ=f+s_1 \cos \delta=1.76953+6.63488 \cos 52.5°=5.80859 \text{ mm}$$

$$PF=\frac{GP^2}{4f}=\frac{QC^2}{4f}=\frac{5.26380^2}{4\cdot 1.176953}=3.91454 \text{ mm} \quad [12]$$

$$s_3=PC-PF=5.80859 \text{ mm}-3.91454 \text{ mm}=1.89405 \text{ mm}$$

$$\eta=\phi+\theta/2=30°+22.5°=52.5°$$

$$s_4^2=s_3^2+s_1^2-2s_3s_1 \cos \eta=1.89405^2+6.63488^2-2(1.89405)(6.63488)\cos 52.5°.$$

Therefore: $s_4 = 5.68407$ mm.

The ellipse parameters are:

$$2a = s_3 + s_4 = 1.89405 + 5.68407 = 7.57812 \text{ mm}$$

$a = 3.78906$ mm; and $$b = \left(a^2 - \left(\frac{s_1}{2}\right)^2\right)^{0.5} = 1.83073 \text{ mm} \quad 2b = 3.66146 \text{ mm}.$$

b. The Small NA Case ($\phi < \theta/2$) and Medium NA Case ($\phi = \theta/2$)

(Second Solution)

The methods shown in the preceding section are straightforward but may result in large devices (for the case shown, a 1 mm diameter input cross section requires about a 1 cm corner turner). A much more compact approach may result from: (1) Using prior-art methods to increase the NA of the input beam to 1.0 or to any other desired large number so that the beam meets the requirements of the large NA corner turner designs; (2) Using a large-NA corner turner to achieve the desired rotation; and (3) Using a copy of the input concentrator, in reverse, to bring the beam back to an output NA matching the input NA. Reversing a non-imaging concentrator to achieve efficient reduction of NA is a well know method but has not been used with corner turners.

Figure 4:
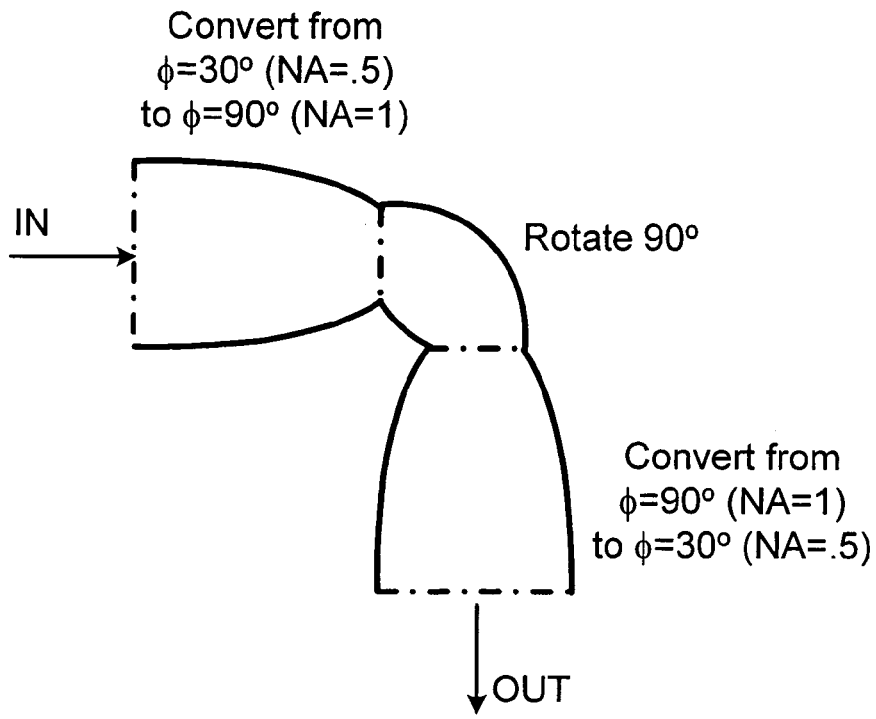
FIG. 4 is a diagram illustrating a 90 degree corner turner for ϕ=30 degrees.

FIG. 4 illustrates this method for the case where $\theta = 90$ degrees and $\phi = 30$ degrees. The 90° rotation section is based on the design of FIG. 1G. This section is actually larger than necessary. This design produces a 180 degree fan of rays which do not strike the outside of the incoming CPC. In the present application, the output of the turning section is immediately captured by the output CPC. Thus, the simple circular-arc reflector design first shown in FIG. 1B can be extended to meet the present need, as shown in FIG. 4A, which eliminates the lower elliptical section of FIG. 4 and replaces the upper elliptical section with a circular arc.

Figure 4A:
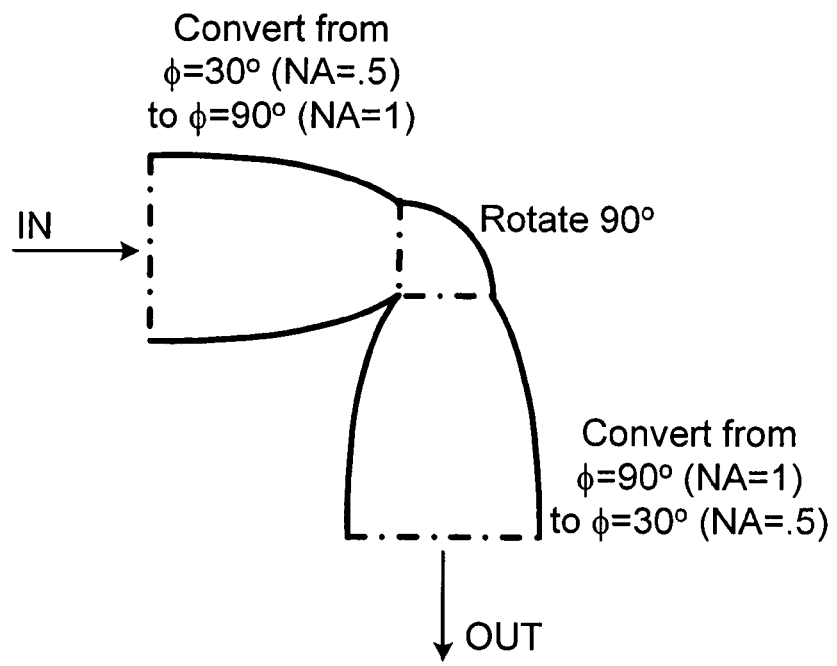
FIG. 4A is a diagram illustrating a compact 90 degree corner turner for ϕ=30 degrees.

If the device of FIG. 4A is fabricated as molded plastic or glass and reflectively coated on the outside, the sharp inside corner of the bend could be difficult to form and coat. Consequently, it is recommended in that case to open up the corner just enough to permit easy fabrication, so that a modified version of FIG. 4 would be appropriate. If the device of FIG. 4A is made as a hollow part, with the reflective coating on the inside, the device is usable just as shown.

Figure 4B:
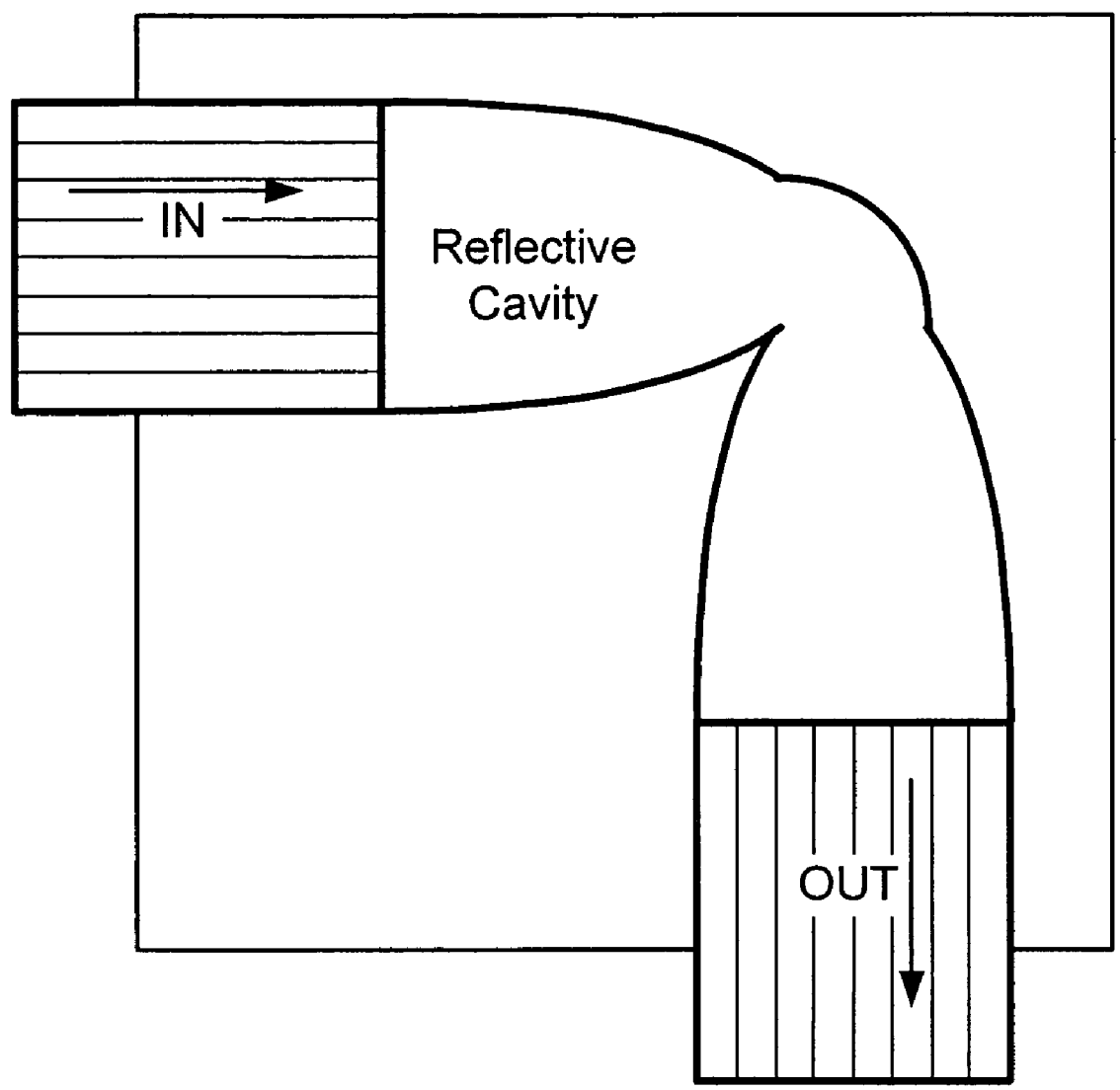
FIG. 4B is a diagram illustrating the use of the design of FIG. 4A to join two fiber bundles.

FIG. 4B is simply FIG. 4A adapted to join two fiber bundles.

3D Embodiments

Figure 5A:
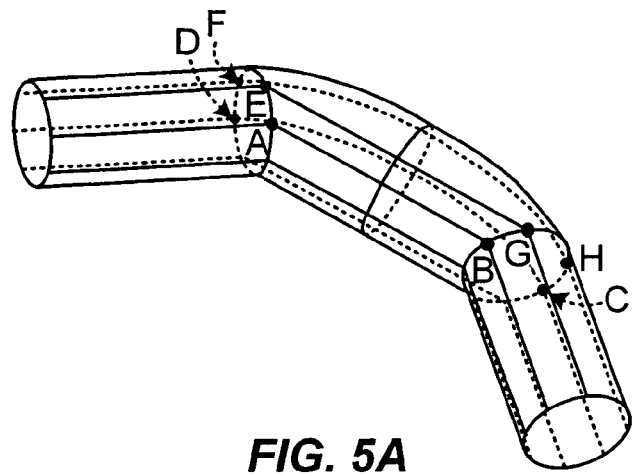
FIG. 5 is a diagram showing a 3D corner turner, constructed by a method similar to that used to construct the 2D corner turner of FIGS. 1I, 1J, and 2.
Figure 5B:
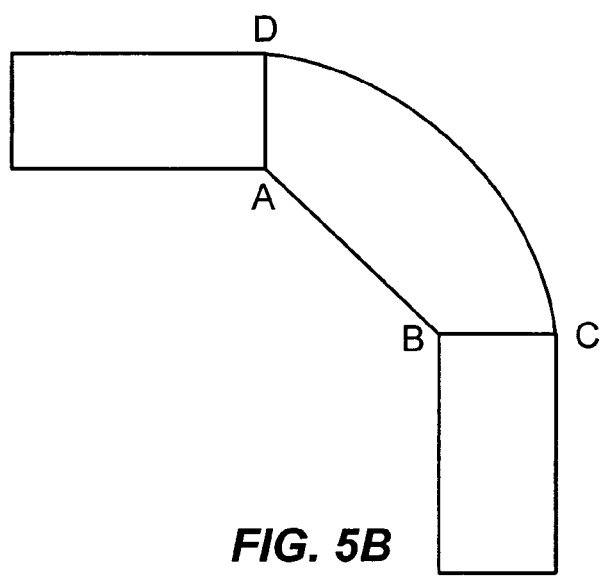
Figure 5C:
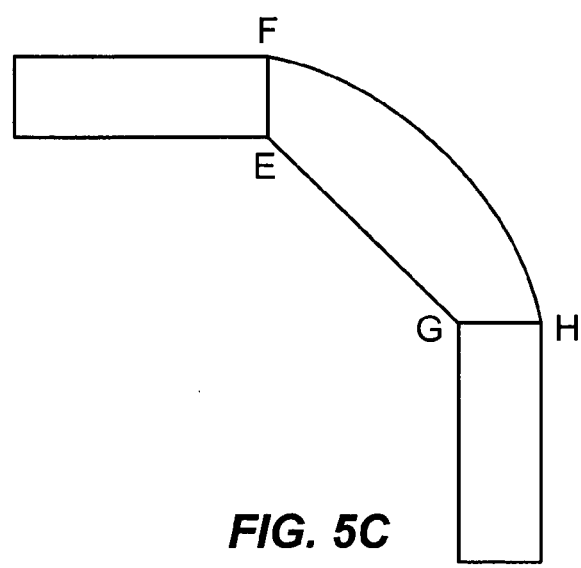

FIG. 5 shows a 3D corner turner, constructed by a method similar to that used to construct the 2D corner turner of FIGS. 1I, 1J, and 2. The realization of this embodiment takes advantage of the recognition that most of the corner turner embodiments described above can be made of any convenient length. Thus, in FIG. 1E, distance BC may be of any length. In FIG. 1I, line BC must be of a certain minimum length, to ensure that no rays will enter the output fiber at angles exceeding the maximum which the fiber can carry without excessive loss, but if section BC is made longer, this is acceptable. The strategy for designing a "low-NA" 3D corner turner to match input and output fibers of circular cross section is as follows:

1. In the median plane of the bend, lay out the boundaries of the reflective channel exactly as was done for the device of FIG. 1I, as shown in FIG. 5B.

2. In planes above or below the median plane of the bend, perform the analogous construction, except that the inner straight-line surface, such as EG, is simply constructed as a straight line between corresponding points on the circular cross sections of input and output fibers.

An analogous procedure, not shown, may be used to construct medium-NA and low-NA 3D corner turners analogous to the 2D corner turners of FIGS. 3 and 4. A similar process, also not shown, may be used to construct a 3D corner turner analogous to the 2D NA=1 devices of FIGS. 1B and 1E. Where the 2D designs call for 2D CPCs, the well-known 3D CPC, which is a figure of rotation of the 2D CPC, would be used instead.

It is known that while 2D CPCs conserve étendue completely, 3D CPCs do not, because of their imperfect handling of skew rays (cf. Chapter 4 of Welsford and Winston, op. cit.). It may be that, similarly, the 3D corner turners of the present invention, do not perfectly conserve étendue, even though the 2D corner turners from which they are derived are conservative of étendue. Even in this case, the 3D corner turners should be useful, because of their compactness and because they avoid the losses created when fiber optics are bent around corners.

The devices described herein have all been characterized by simple conic-section shapes which could be analytically determined. It is known that many types of optical systems can function as well or better when bounded by more complex shapes, which are typically defined by a computer optimization process so as to maximize desired performance parameters. It is likely that the application of known computerized optimization methods to the corner turners described herein, and especially to the 3D versions, will provide alternative boundary forms which do as well or better than the simple analytic forms described herein, with respect to such measures as étendue conservation. Such computer optimization is contemplated within the scope of the invention.

Several of the embodiments described herein have employed CPCs to transform beams of low NA to beams whose NA is 1.0. Wherever a CPC has been described, it is also contemplated to use such devices as the modified CPC shown in FIG. 5.4 of Welford and Winston, op. cit., to produce beams of NA somewhat less than 1, for use in analogous structures. Corner turner systems using such modified CPCs, or other optical concentrators having output NA somewhat less than 1.0, may be advantageous in producing more easily fabricated corner turner structures, e.g. structures which do not require elliptical surfaces on the inner sides of corners.

The properties of corner turner designs described herein have been discussed on the assumption that all reflective surfaces are perfect specular reflectors, matching perfectly their mathematically ideal shapes. As is ordinary in the practice of optical design, real surfaces will not achieve such perfection, so that the actual efficiency of devices according to this invention will be less than ideal.

Throughout this document there are many references to reflective surfaces. Such surfaces may be any type of reflecting surfaces known to those skilled in optical design, including but not limited to metallized surfaces, surfaces coated with dielectric or metal/dielectric reflectors, and totally internally reflecting surfaces.

Additionally, throughout this document, there are many references to the use of optical fibers in combination with non-imaging corner turners. In all of these cases, the optical fibers may be of any known optical material, including but not limited to glass or plastic, may be solid or hollow, and may be single fibers or multiple fiber bundles. The fibers may be held in the proper spatial relationship to the corner turners by any known means, including but not limited to mechanical fixturing and gluing. Especially with plastic optical fibers, it may be advantageous to form a non-imaging corner turner integrally upon the end of the fiber, using either added material or the material of the fiber itself.

In one application, a first corner turner 702 is used to direct light to a patient 706, such as for pulse oximetry. The first corner turner 702 receives light of a small NA from the fiber optic 704. A second corner turner 708 is used to provide reflected light from the patient 708 to a return fiber optic 710, and receives large NA input light and provides it to the smaller NA return fiber optic 710. The fiber optic cross section could be either rectangular, or circular, and the fiber optic may comprise either a single large fiber or a bundle of smaller fibers.

In another application, non-collinear integrated optical waveguides on a planar substrate are interconnected when they meet at corners by 2D optical corner turners according to the present invention.

In yet another application, patch panels for interconnection of plastic optical communication fibers are made more compact by the use of 3D corner turners according to the present invention, to facilitate right-angle turns of signal carriers behind the patch panel. The devices used to make such right-angle turns would have an external appearance similar to the right-angle electrical connectors that are commonly used to permit compact patching of such electrical connection means as BNC coaxial cables.

FIG. 6 illustrates another family of embodiments of the invention, in which, surprisingly, étendue conservation can be achieved without requiring any curved surfaces. The key phenomenon exploited here is that the reflectivity of an interface between materials of different refractive index (i.e., Fresnel reflection) depends strongly on angle of incidence.

Figure 6A:
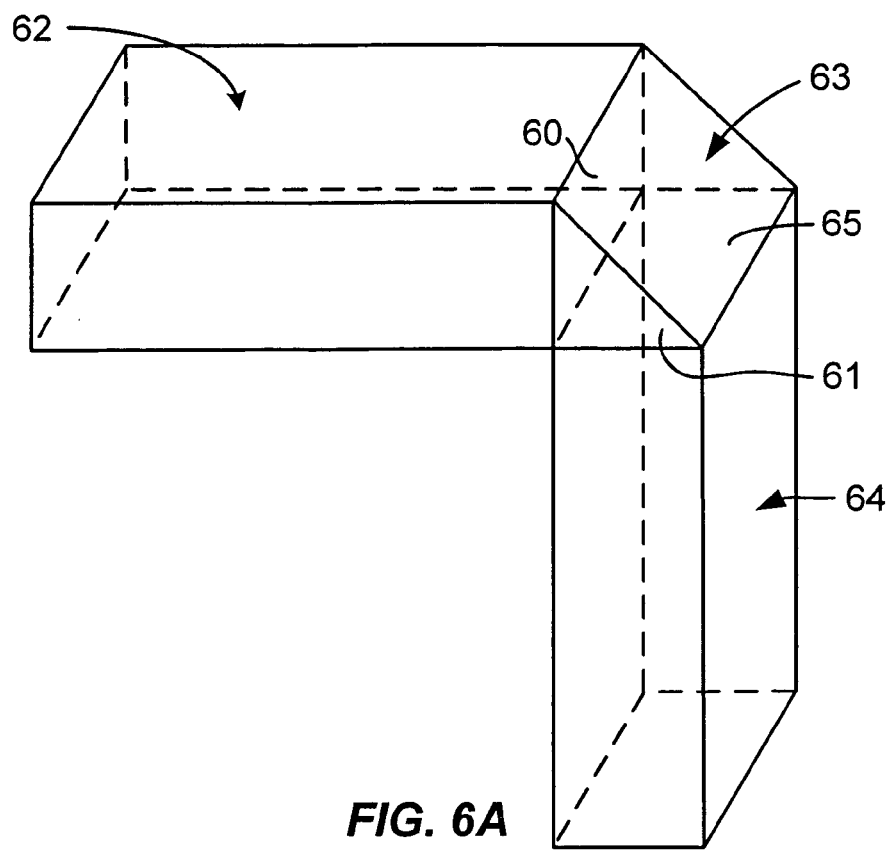
FIG. 6 is a diagram showing a corner turner using special interface properties.

In FIG. 6A, input light guide 62 brings light to corner turning prism 63, which redirects this light into output light guide 64. The interface between guide 62 and prism 63 is surface 60, and the interface between prism 63 and guide 64 is surface 61. The numerical apertures of light guides 62 and 64 are assumed to be equal in order to simplify this example (although, in general, they may be different), and the refractive indices of their core material (which might, for example, be glass, plastic, or air) are also assumed to be equal (although, in general, they may be different) so that the maximum angles of confined rays, with respect to the optical axis, are equal in the two light guides. It is necessary for the corner turning structure 63 to so direct rays from input guide 62 so that all of them fall within the maximum confinement angle of output guide 64.

Figure 6B:
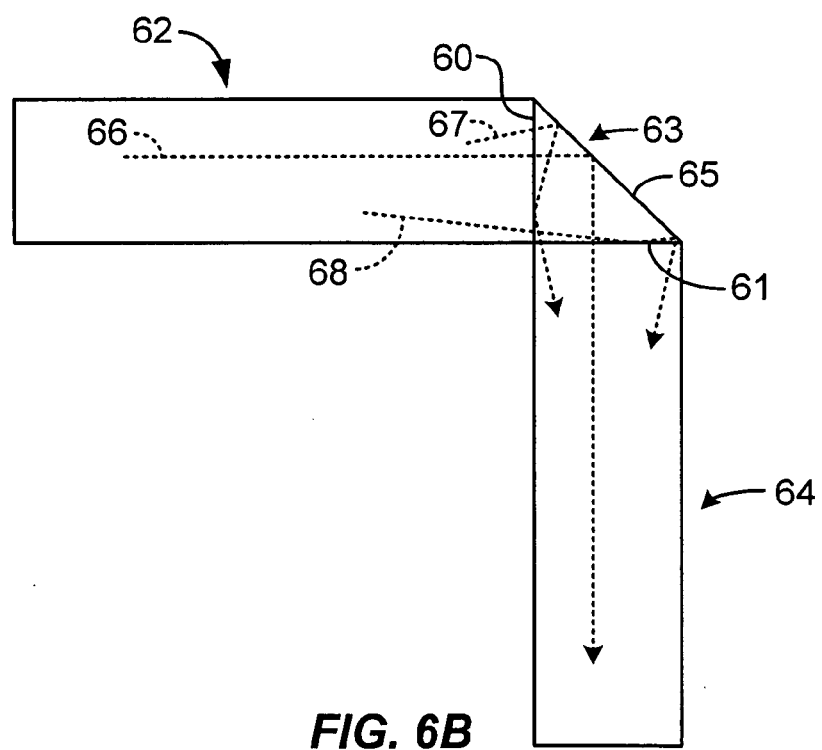
Figure 7:
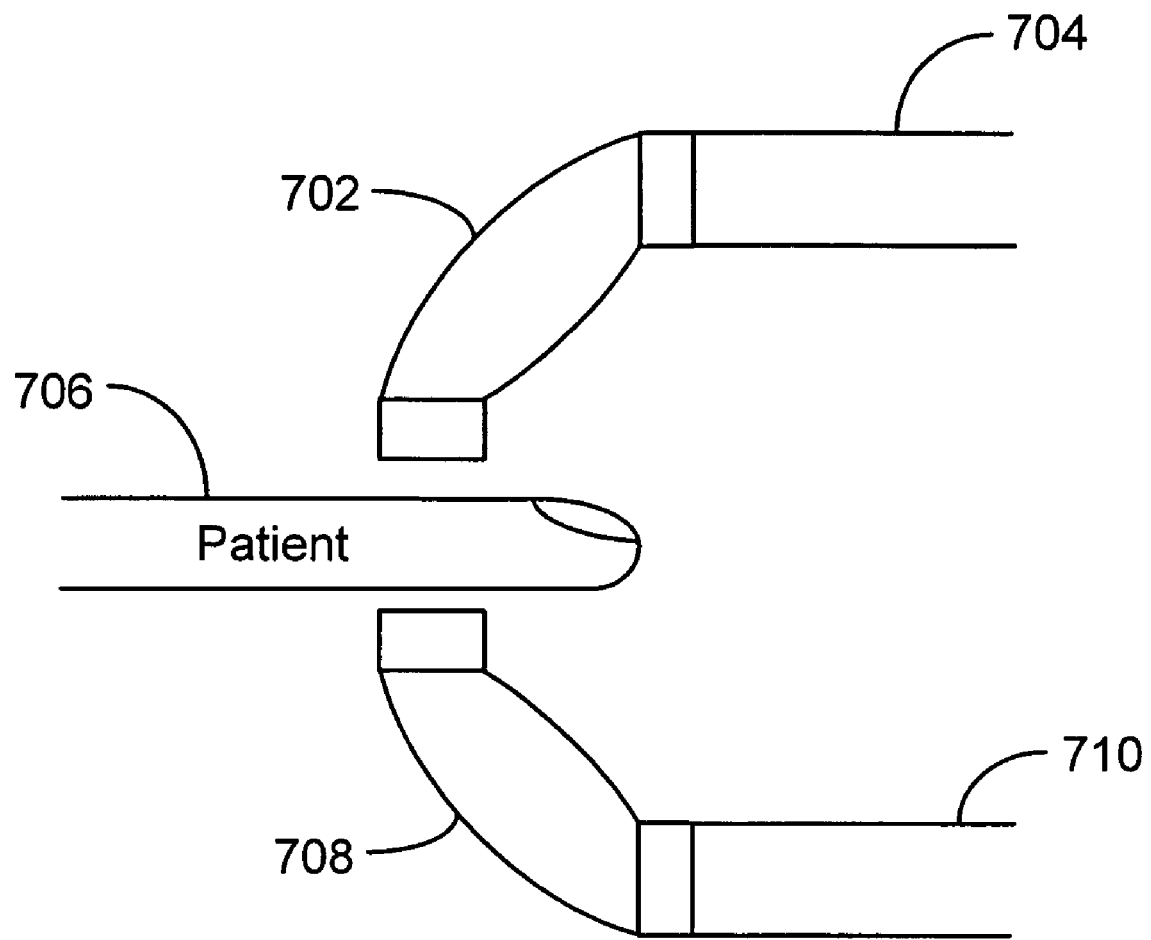
FIG. 7 is a diagram showing an application of the corner turner used to direct light to a patient from an optical fiber and to direct light collected from a patient to a return fiber.

Tilted surface 65 is arranged to reflect axial rays from guide 62 into the axis of guide 64. Then, automatically, all other rays reflected from surface 65 are reflected within the confinement range of guide 64. Another important condition needs to be met to accomplish étendue—conserving corner turning—all rays passing through the area of interface 60 must be delivered within the area of interface 61. An equivalent condition was violated in the system of FIG. 1 in which a flat reflector was shown to fail as an efficient corner turner. A key innovation in the construction of the FIG. 6 embodiment is that we provide for rays which strike interfaces 60 or 61 close to normal incidence to be transmitted with high probability, while rays which strike these interfaces far from normal incidence are reflected with high probability. The paths of several rays are illustrated in FIG. 6B in order to demonstrate how the necessary confinement is achieved. Ray 66, which is nearly normal to surface 60, passes through with only the small Fresnel reflection loss characteristic of normal incidence rays striking a dielectric interface. Ray 67 is close enough to normal incidence to pass through surface 60 with small loss, but upon return from reflection at surface 65, it strikes interface 60 at an angle far enough from normal to be reflected, so as to enter light guide 64 through interface 61. Ray 68 passes through interface 60 at close to normal incidence. It is then reflected in its first interaction with interface 61 because of its far-from-normal incidence, and then passes through surface 61 upon reflective return from surface 65. Were it not for the reflections undergone at surfaces 60 and 61 respectively, rays 67 and 68 would be lost to the system.

One way to produce the desired angle-dependent reflection properties at interfaces 60 and 61 is to provide multi-layer dielectric coatings, designed by methods well known to thin film coating designers, at these interfaces. Another way is simply to choose the material of prism 63 to have a refractive index sufficiently higher than that of guides 62 and 64 so that the necessary confinement is achieved by simple Fresnel reflection.

For example, if the core material of guides 62 and 64 has refractive index $n_1=1.41$ and the material of prism 63 has refractive index $n_2=1.51$, the critical angle of incidence on the interface between the two materials, measured from the high-index side, is given by $$\phi_c = \arcsin\left(\frac{n_1}{n_2}\right)$$

which for this particular material pair has the result $\phi_c=69°$. Any ray from the high-index side will be totally internally reflected whose angle to the normal of the interface exceeds 69°. Considering rays which come from input guide 62 and reflect from prism surface 65, any rays which have an angle of less than 21° to the optical axis of exit guide 64, after reflection, will be properly conditioned to reflect from interface 60 if they strike it. The corresponding numerical aperture of the reflected beam, in the medium of prism 63, is given by:

$$NA = n_2 \sin \phi_{max2}$$

which in this example results in NA=0.54. Thus, if the afferent and efferent light guides, 62 and 64, have NA of 0.54 or less, total reflection at interfaces 60 and 61 will suffice to deliver the input light beam to guide 64 without loss of power.

In select embodiments, the non-imaging optical concentrator may be a compound parabolic concentrator (CPC) or any other optical concentrator known in the art. In particular embodiments, CPCs are depicted herein as illustrative and not limiting. It will be obvious to one skilled in the art that other configurations of optical concentrators may be used herein without deviating from the spirit of the invention.

What is claimed is:

1. An apparatus for deflecting light from an optical fiber around a corner, comprising:
   a light guide configured to transmit light;
   a corner turning optical structure coupled to the light guide at an interface, wherein the corner turning optical structure includes a surface angled with respect to the interface such that axial light rays that pass through the interface from the light guide are reflected by the surface into a window of the corner turning optical structure at an angle substantially normal to the window, and wherein the interface is configured for total internal reflection of light rays which strike the interface from the corner turner at an angle of incidence that is greater than a defined critical angle, wherein the critical angle is 69 degrees or more.

2. The apparatus of claim 1 wherein a core of the light guide has a first refractive index, $n_1$, and the corner turning optical structure is comprised of a body of material having a second refractive index, $n_2$, wherein $n_2$ is greater than $n_1$.

3. The apparatus of claim 1 wherein the interface comprises a single-layer or multi-layer dielectric coating configured to define the critical angle.

4. The apparatus of claim 1 further comprising a second light guide, and a second interface defined between the second light guide and the corner turning optical structure, wherein the second interface includes the window.

5. The apparatus of claim 4, wherein a single-layer or multi-layer dielectric coating is applied to the second interface, the single-layer or multi-layer dielectric coating configured to define a critical angle of the second interface.

6. The apparatus of claim 4, wherein the second light guide has a core having a refractive index, $n_3$ and the corner turning structure has a refractive index of $n_2$, wherein $n_2$ is greater than $n_3$.

7. An apparatus for deflecting light around a corner, comprising:
an optical light guide configured to transmit a beam of light at a maximum divergence half-angle less than 90 degrees; and
an optical corner-turning structure adjoining the optical light guide to form an interface, wherein the corner-turning structure is adapted to reflect axial light from the optical light guide off of a surface of the corner-turning structure, the surface arranged to direct the axial light into a window of the optical corner-turning structure at a substantially normal incidence to the window, wherein the surface is configured to reflect light entering the corner-turning structure from the interface at an angle that is a defined degree away from normal to the interface back toward the interface, and wherein the interface is configured for total internal reflection of light striking the interface from within the corner-turning structure at an angle greater than a defined critical angle, wherein the critical angle is 69 degrees or greater.

8. The apparatus of claim 7 wherein the corner-turning structure comprises a plurality of reflective optical surfaces configured to direct light to pass through the window.

9. The apparatus of claim 7 wherein the interface is configured to transmit a majority of light rays received from the light guide and reflect a majority of light rays incident from the corner turning structure.

10. The apparatus of claim 7 wherein the interface comprises a thin-film dielectric coating, wherein the thin-film dielectric coating is configured to define the critical angle.

* * * * *